United States Patent
Gonen et al.

(10) Patent No.: US 11,033,524 B2
(45) Date of Patent: Jun. 15, 2021

(54) METHODS AND COMPOSITIONS FOR TREATING DISORDERS ASSOCIATED WITH CORTICO-HIPPOCAMPAL HYPERACTIVITY

(71) Applicant: RAMOT AT TEL-AVIV UNIVERSITY LTD., Tel-Aviv (IL)

(72) Inventors: Nir Gonen, Tel-Aviv (IL); Boaz Styr, Tel-Aviv (IL); Eytan Ruppin, Tel-Aviv (IL); Inna Slutsky, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 16/462,027

(22) PCT Filed: Nov. 23, 2017

(86) PCT No.: PCT/IL2017/051282
§ 371 (c)(1),
(2) Date: May 17, 2019

(87) PCT Pub. No.: WO2018/096538
PCT Pub. Date: May 31, 2018

(65) Prior Publication Data
US 2019/0269644 A1 Sep. 5, 2019

Related U.S. Application Data

(60) Provisional application No. 62/425,936, filed on Nov. 23, 2016.

(51) Int. Cl.
| | |
|---|---|
| C12N 15/113 | (2010.01) |
| A61K 31/277 | (2006.01) |
| A61P 25/08 | (2006.01) |
| A61K 9/00 | (2006.01) |
| A61K 31/713 | (2006.01) |
| C12N 15/86 | (2006.01) |
| A61P 25/28 | (2006.01) |
| A61K 31/7105 | (2006.01) |
| A61K 45/06 | (2006.01) |
| A61K 31/7072 | (2006.01) |
| A61K 31/42 | (2006.01) |

(52) U.S. Cl.
CPC .......... *A61K 31/277* (2013.01); *A61K 9/0019* (2013.01); *A61K 31/42* (2013.01); *A61K 31/7072* (2013.01); *A61K 31/713* (2013.01); *A61K 31/7105* (2013.01); *A61K 45/06* (2013.01); *A61P 25/08* (2018.01); *A61P 25/28* (2018.01); *C12N 15/113* (2013.01); *C12N 15/86* (2013.01)

(58) Field of Classification Search
None
See application file for complete search history.

(56) References Cited

U.S. PATENT DOCUMENTS

| 5,556,870 A | 9/1996 | Weithmann et al. | |
| 2010/0028297 A1* | 2/2010 | Stewart | A61K 45/06 424/85.4 |

FOREIGN PATENT DOCUMENTS

WO 2009133141 A2 11/2009

OTHER PUBLICATIONS

Fang et al; "Dihydroorotate dehydrogenase depletion hampers mitochondrial function and osteogenic differentiation in osteoblasts" European Journal of Oral Sciences vol. 124, Issue 3 pp. 241-245. (2016).
Herrmann et al; "Leflunomide: an immunomodulatory drug for the treatment of rheumatoid arthritis and other autoimmune diseases" Immunopharmacology vol. 47, Issues 2-3, pp. 273-289. (2000).
Khachanova et al; "Extending the Potential of the Treatment of Multiple Sclerosis with a New Agent for Oral Use—Teriflunomide (Aubagio)"Neuroscience and Behavioral Physiology vol. 47, pp. 112-116 (2017).
Merrill et al; "Teriflunomide reduces behavioral, electrophysiological, and histopathological deficits in the Dark Agouti rat model of experimental autoimmune encephalomyelitis" Journal of Neurology vol. 256, pp. 9-103 (2009).
Spodnik et al; "Mechanism of leflunomide-induced proliferation of mitochondria in mammalian cells" Mitochondrion vol. 2, Issue 3, pp. 163-179 (2002).
Extended Search Report issued in EP application No. EP17873294. 7, dated Jun. 23, 2020.
International Preliminary Report on Patentability received in PCT Application No. PCT/IL2017/051282, dated Jun. 6, 2019.
Bakker et al; "Reduction of Hippocampal Hyperactivity Improves Cognition in Amnestic Mild Cognitive Impairment" Neuron, 74, pp. 467-474. (2012).
Berchtold et al; "Brain gene expression patterns differentiate mild cognitive impairment from normal aged and Alzheimer's disease" Neurobiology of Aging 35 pp. 1961-1972. 2014).
Bough et al; "Mitochondrial biogenesis in the anticonvulsant mechanism of the ketogenic diet. Annals of Neurology", 60, pp. 223-235. (2006).

(Continued)

*Primary Examiner* — J. E. Angell
(74) *Attorney, Agent, or Firm* — Knobbe Martens Olson & Bear, LLP

(57) ABSTRACT

The present invention provides pharmaceutical compositions and methods for preventing, delaying onset of, or treating diseases or disorders associated with cortico-hippocampal hyperactivity such as epilepsy, using an active agent capable of reducing dihydroorotate dehydrogenase (DHODH) enzyme activity in the central nervous system, optionally together with a pyrimidine nucleobase or an intermediate in the de novo synthesis thereof.

15 Claims, 13 Drawing Sheets

Specification includes a Sequence Listing.

(56) References Cited

OTHER PUBLICATIONS

Eid et al; "Loss of glutamine synthetase in the human epileptogenic hippocampus: possible mechanism for raised extracellular glutamate in mesial temporal lobe epilepsy". The Lancet, 363, pp. 28-37. (2004).

Garriga-Canut et al; "2-Deoxy-D-glucose reduces epilepsy progression by NRSF-CtBP-dependent metabolic regulation of chromatin structure". Nature Neuroscience, 9, pp. 1382-1387. (2006).

Henry et al; "Quantifying interictal metabolic activity in human temporal lobe epilepsy". Journal of Cerebral Blood Flow & Metabolism, 10, pp. 748-757. (1990).

Lutas et al; "The ketogenic diet: metabolic influences on brain excitability and epilepsy". Trends in Neurosciences, 36, pp. 32-40. (2013).

Petroff et al; "Glutamate—glutamine Cycling in the Epileptic Human Hippocampus" Epilepsia, 43, pp. 703-710 . (2002).

Sada et al; "Targeting LDH enzymes with a stiripentol analog to treat epilepsy". Science 347, pp. 1362-1367. (2015).

Sanchez et al; "Levetiracetam suppresses neuronal network dysfunction and reverses synaptic and cognitive deficits in an Alzheimer's disease model" Proceedings of the National Academy of Sciences,109,pp. E2895-E2903. (2012).

Petzer et al; "Leflunonnide, a reversible monoamine oxidase inhibitor." Central Nervous System Agents in Medicinal Chemistry vol. 16 Issue 2.

Pesini et al. "OXPHOS, pyrimidine nucleotides, and Alzheimer's disease: a pharmacogenomics approach." Journal of Alzheimer's Disease 42.1 : pp. 87-96.(2014).

Oh et al; "Teriflunomide" American Academy of Neurology pp. 254-259. (2013).

International Search Report and Written Opinion received in PCT Application No. PCT/IL2017/051282, dated Feb. 26, 2018.

\* cited by examiner

METHODS AND COMPOSITIONS FOR TREATING DISORDERS ASSOCIATED WITH CORTICO-HIPPOCAMPAL HYPERACTIVITY

CROSS REFERENCE TO RELATED APPLICATIONS

This application is the U.S. National Phase under 35 U.S.C. § 371 of International Application No. PCT/IL2017/051282 filed Nov. 23, 2017, designating the U.S. and published as WO 2018/096538 on May 31, 2018, which claims the benefit of U.S. Provisional Application No. 62/425,936 filed Nov. 23, 2016. Any and all applications for which a foreign or domestic priority claim is identified above and/or in the Application Data Sheet as filed with the present application are hereby incorporated by reference under 37 CFR 1.57.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 30732058_1.TXT, the date of creation of the ASCII text file is Jun. 13, 2019, and the size of the ASCII text file is 2.27 KB.

TECHNICAL FIELD

The present invention relates to methods and pharmaceutical compositions for preventing, delaying onset of, or treating diseases or disorders associated with cortico-hippocampal hyperactivity, more particularly, for treating epilepsy or preventing sudden unexplained death in epilepsy.

BACKGROUND ART

Emerging evidence suggests that hyperactivity of hippocampal and medial temporal lobe network is common in humans with temporal lobe epilepsy (TLE) (Pitkanen and Sutula, 2002), mild-cognitive impairments (MCI) (Bakker et al., 2012; Dickerson et al., 2005; Yassa et al., 2010), in mildly impaired, amyloid positive older adults (Sperling et al., 2009) and young APOE-ε4 carriers at genetic risk for Alzheimer's disease (AD) (Kunz et al., 2015). Further, a longitudinal fMRI study revealed that hippocampal hyperactivation in MCI predicted a greater degree of subsequent cognitive decline (Miller et al., 2008). Hippocampal hyperactivity is evident in numerous epilepsy animal models (Grone and Baraban, 2015; Krook-Magnuson and Soltesz, 2015; Paz and Huguenard, 2015), AD mouse models (Busche et al., 2008; Minkeviciene et al., 2009; Palop et al., 2007; Palop and Mucke, 2009; Verret et al., 2012) and cognitively-impaired aged rats (Koh et al., 2010). Notably, a low-dose of the anti-epileptic drug levetiracetam reduces metabolic hyperactivity in the hippocampus and mediates the improvement of memory in MCI patients (Bakker et al., 2012). Similarly, leviteracetam reduces brain hyperactivity and improves cognitive impairments in AD mouse models (Sanchez et al., 2012). However, all the other anti-epileptic drugs show no efficiency in attenuation of AD-related brain hyperactivity (Sanchez et al., 2012).

Despite the development of various antiepileptic drugs over the past 20 years, the efficacy of drug treatments for epilepsy has not substantially improved, and 25-40% of the patients suffer from drug-resistant seizures (Wilcox et al., 2013). New antiepileptic strategies are thus urgently needed to improve the quality of life and prevent premature deaths of patients with epilepsy. For AD patients, the impact of the currently approved FDA drugs on the disease manifestations is modest and even negligible. Over 300 different pharmacological compounds, most of which are designed to reduce Aβ levels and its aggregation, are at various stages of development; however, until now clinical trials focused on anti-Aβ therapies fail to show improvements of cognitive function. Thus, new therapeutic approaches aimed at reducing excitability, decreasing excitation-inhibition ratio and increasing stability of firing patterns, may be particularly beneficial for the treatment of epilepsy, MCI and early AD stages.

A recent study suggests that gene expression patterns in MCI are neither an extension of aging nor an intermediate between aging and AD, but represent a unique molecular state undergoing a nonlinear progression in the transitions from cognitively intact aging to MCI and AD (Berchtold et al., 2014). The MCI brain undergoes vast molecular reprogramming, resulting in upregulation of metabolic genes related to mitochondrial bioenergetics, mitochondrial electron transport chain (mECT) reaction, protein homeostasis and synaptic function (Berchtold et al., 2014). Gene expression changes that potentiate neuronal excitability and synaptic activity in limbic brain regions were strongly associated with impaired cognitive function. Moreover, robust changes in metabolism have been observed in epilepsy, even at the very early stages of the disease: diminished utilization of glucose (Henry et al., 1990) and shifts in glutamate metabolism were connected to the progression of the disease (Eid et al., 2004; Petroff et al., 2002). The ketogenic diet was found to be highly effective in treating epilepsy, emphasizing the importance of modifications in the metabolic network in rescuing or diminishing seizure activity (Bough et al., 2006; Lutas and Yellen, 2013). Perturbations in metabolism such as inhibition of lactate dehydrogenase (Sada et al., 2015) and inhibition of glycolysis (Garriga-Canut et al., 2006) have been shown to reduce seizure activity.

SUMMARY OF INVENTION

It has now been found, in accordance with the present invention, that the dihydroorotate dehydrogenase (DHODH) enzyme is a critical regulator of neuronal excitability and inhibition-excitation balance in hippocampal circuits, and inhibition of this enzyme, either by a small molecule, e.g. an inhibitor such as (2Z)-2-cyano-3-hydroxy-N-[4-(trifluoromethyl) phenyl]but-2-enamide (teriflunomide; Teri; Aubagio®), or a small interfering RNA (siRNA)- or small/short hairpin RNA (shRNA)-knockdown, may represent a new strategy to reduce/attenuate cortico-hippocampal hyperactivity, to thereby prevent, delay onset of, or treat neurodegenerative diseases and disorders associated with elevated cortico-hippocampal activity such as epilepsy, and prevent or delay MCI-to-AD progression.

The protein encoded by the DHODH gene, a mitochondrial protein located on the outer surface of the inner mitochondrial membrane, catalyzes the fourth enzymatic step, i.e., the ubiquinone-mediated oxidation of dihydroorotate to orotate, in the de novo pyrimidine biosynthesis. Surprisingly, as further been found, addition of uridine (a precursor of pyrimidines) does not occlude the reduction in maximum firing rate (MFR) induced by teriflunomide at a timescale of 2 days, indicating that lack of uridine is not the factor leading to long-term reduction in the MFR, and suggesting that DHODH inhibition triggers a long-term reduction in firing rates due to its direct inhibition of mitochondrial functions, but not de-novo pyrimidine synthesis.

In one aspect, the present invention thus relates to a method for preventing, delaying onset of, or treating a disease or disorder associated with cortico-hippocampal hyperactivity in a subject, e.g., a mammal such as a human, in need thereof, said method comprising administering to said subject a therapeutically effective amount of an active agent capable of reducing DHODH enzyme activity in the central nervous system (CNS) of said subject, optionally together with a pyrimidine nucleobase or an intermediate in the de novo synthesis thereof, provided that when said active agent is administered without said pyrimidine nucleobase or intermediate in the de novo synthesis thereof, said subject does not suffer from multiple sclerosis. The active agent capable of reducing DHODH enzyme activity in the CNS may be, e.g., a nucleic acid molecule capable of reducing the gene expression level of DHODH enzyme, or a small molecule capable of reducing the activity of DHODH enzyme in the CNS.

In another aspect, the present invention relates to an active agent capable of reducing DHODH enzyme activity in the CNS for use, optionally in combination with a pyrimidine nucleobase or an intermediate in the de novo synthesis thereof, in preventing, delaying onset of, or treating a disease or disorder associated with cortico-hippocampal hyperactivity.

It yet another aspect, the present invention provides a pharmaceutical composition for preventing, delaying onset of, or treating a disease or disorder associated with cortico-hippocampal hyperactivity, said composition comprising an active agent capable of reducing DHODH enzyme activity in the CNS, and optionally a pyrimidine nucleobase or an intermediate in the de novo synthesis thereof.

In still another aspect, the present invention provides a pharmaceutical composition comprising an active agent capable of reducing DHODH enzyme activity in the CNS, and a pyrimidine nucleobase or an intermediate in the de novo synthesis thereof.

In a further aspect, the present invention provides a kit comprising: (i) a first pharmaceutical composition comprising an active agent capable of reducing DHODH enzyme activity in the CNS; (ii) a second pharmaceutical composition comprising a pyrimidine nucleobase or an intermediate in the de novo synthesis thereof; and optionally (iii) instructions for co-administration of said pharmaceutical compositions for preventing, delaying onset of, or treating a disease or disorder associated with cortico-hippocampal hyperactivity.

In yet a further aspect, the present invention relates to a method for treatment of multiple sclerosis in a subject in need thereof, said method comprising intrathecally administrating to said subject a therapeutically effective amount of an active agent capable of reducing DHODH enzyme activity in the CNS of said subject, e.g., teriflunomide or a pharmaceutically acceptable salt thereof.

In still a further aspect, the present invention relates to an active agent capable of reducing DHODH enzyme activity in the CNS, e.g., teriflunomide or a pharmaceutically acceptable salt thereof, for use in treatment of multiple sclerosis, wherein said active agent is formulated for intrathecal administration.

DETAILED DESCRIPTION

Figure 1A:
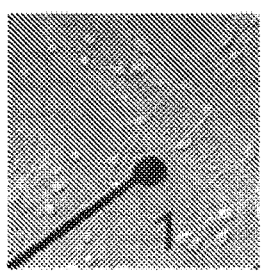
FIGS. 1A-1H show that DHODH inhibition induces a reduction of neuronal firing rates. (1A) A single electrode from a multi-electrode array of 64, with surrounding neurons; (1B) Example of recorded data from one channel with threshold detection of spiking activity. Lower panel showing spike time signatures. Bars: 50 ms/20 μV. (1C) Waveforms from extracted spikes in 1B. Bars: 20 μV/1 ms. (1D-1F) Raster plots of spike times from baseline (1D), from DHODH knockdown (KD) baseline (1E), and after 4 h application of 50 uM teriflunomide (1D and 1F are from the same culture). (1G) MFR of the network is reduced after application of 50 μM teriflunomide on control, but not in DHODH KD culture. (1H) Average MFR of teriflunomide application. Teriflunomide did not have a significant effect on DHODH KD culture (n=5 experiments for control, n=4 experiments for KD). ****p<0.0001 using non-parametric Student's t-test.

In one aspect, the present invention relates to a method for preventing, delaying onset of, or treating a disease or disorder associated with cortico-hippocampal hyperactivity in a subject in need thereof, said method comprising administering to said subject a therapeutically effective amount of an active agent capable of reducing DHODH enzyme activity in the CNS of said subject, optionally together with a pyrimidine nucleobase or an intermediate in the de novo synthesis thereof, provided that when said active agent is administered without said pyrimidine nucleobase or intermediate in the de novo synthesis thereof, said subject does not suffer from multiple sclerosis.

The term "cortico-hippocampal hyperactivity" as used herein refers to an increase in the neuronal excitability and synaptic transmission in the cortex and/or hippocampus, i.e., to cortical hyperactivity and/or hippocampal hyperactivity, reflected, e.g., by clinically silent seizures and epileptiform spikes (Lam et al., 2017; Vossel et al., 2013; Vossel et al., 2016).

In certain embodiments, the active agent capable of reducing DHODH enzyme activity in the CNS comprises a nucleic acid molecule capable of reducing the gene expression level of DHODH enzyme. In some particular such embodiments, said nucleic acid molecule is capable of directly reducing the gene expression level of DHODH enzyme. In other particular such embodiments, said nucleic acid molecule is capable of indirectly reducing the gene expression level of DHODH enzyme.

siRNA molecules are short double stranded RNA molecules capable of reducing the expression level of a protein by inhibiting, reducing or eliminating gene expression through degradation of the target mRNA (in case of perfect match) or inhibition of mRNA translation (in case of imperfect match). The siRNA molecules may be artificial siRNA.

The term "shRNA" refers to an artificial double-stranded small hairpin RNA having a stem-loop structure and comprising 19-29 nucleotide. The shRNA is capable of reducing the expression level of a protein by inhibiting, reducing or eliminating gene expression through degradation of the target mRNA (in case of perfect match) or inhibition of mRNA translation (in case of imperfect match).

In certain particular such embodiments, said nucleic acid molecule capable of reducing the gene expression level of DHODH enzyme comprises an artificial and/or isolated siRNA or shRNA molecule comprising a nucleic acid sequence being complementary to a sequence within a nucleic acid sequence encoding said DHODH enzyme, or a nucleic acid molecule encoding said artificial siRNA or shRNA molecule. In some more particular such embodiments, the subject treated by the method of the invention is a human, and said DHODH enzyme is a human DHODH enzyme. In certain such embodiments, the isolated/artificial siRNA or shRNA molecule comprises a nucleic acid sequence having a sequence identity of 90% or more, e.g. about 95% or more, about 98% or more, or about 99%, identity to a sequence within said nucleic acid sequence encoding the DHODH enzyme; or a nucleic acid sequence being perfectly complementary to a sequence within said nucleic acid sequence encoding the DHODH enzyme.

In specific such embodiments, the subject treated by the method of the invention is a human, said DHODH enzyme is a human DHODH enzyme, and said siRNA or shRNA molecule comprises a nucleic acid sequence having 100% match with a sequence within said nucleic acid sequence encoding said human DHODH enzyme, which corresponds to a sequence within the nucleic acid sequence encoding the mouse DHODH enzyme that is selected from SEQ ID NOs. 1-10 (Table 1), e.g., SEQ ID NO. 6 that is exemplified herein.

TABLE 1

| Sequences having perfect match to the mouse DHODH gene | | |
|---|---|---|
| SEQ ID NO. | Clone ID | SEQUENCE |
| 1 | TRCN0000041435 | CGACGGACTGATCATCACAAA |
| 2 | TRCN0000041436 | CGACCATTTCTACGCCGAGTA |
| 3 | TRCN0000287215 | CGACCATTTCTACGCCGAGTA |

TABLE 1-continued

Sequences having perfect match to the mouse DHODH gene

| SEQ ID NO. | Clone ID | SEQUENCE |
|---|---|---|
| 4 | TRCN0000041433 | GCAGACTATGTAGAGGGTGTT |
| 5 | TRCN0000041437 | CGGACTCTATAAGCTGGGCTT |
| 6 | TRCN0000294665 | CCACTGTCTCTAGATCTAAAT |
| 7 | TRCN0000041434 | CCTGGGCCATAAATTCCGAAA |
| 8 | TRCN0000294664 | GAGGACCAAGCTGTTATTAAC |
| 9 | TRCN0000294666 | TGAGCTGGAGGCCCTTCTAAA |
| 10 | TRCN0000294663 | TGGGCTGCCTCTGGGAATAAA |

In other particular such embodiments, said active agent is a vector comprising said nucleic acid molecule. In more particular such embodiments, said vector is a modified virus derived from a virus selected from retrovirus, adenovirus, adeno-associated virus, pox virus, alphavirus, herpes virus, or lentivirus. Certain specific such embodiments are those wherein said vector is a modified virus derived from a lentivirus, i.e., a lentiviral-based shRNA delivery system. In particular such embodiments, said vector comprises a nucleic acid molecule encoding an shRNA molecule comprising a nucleic acid sequence being complementary to a sequence within a nucleic acid sequence encoding said DHODH enzyme.

In certain embodiments, the active agent capable of reducing DHODH enzyme activity in the CNS is a small molecule capable of reducing the activity of said DHODH enzyme in said CNS, i.e., a DHODH inhibitor, or a pharmaceutically acceptable salt thereof. Examples of DHODH inhibitors include, without being limited to, 5-methyl-N-[4-(trifluoromethyl)phenyl]-isoxazole-4-carboxamide (leflunomide) or its metabolite (2Z)-2-cyano-3-hydroxy-N-[4-(trifluoromethyl)phenyl]but-2-enamide (teriflunomide); 6-fluoro-2-[4-(2-fluorophenyl)phenyl]-3-methylquinoline-4-carboxylic acid (brequinar); and 3-(3-chlorophenyl)-6,7-dihydro-5H-benzofuran-4-one (DD264). In particular embodiments the DHODH inhibitor is leflunomide or teriflunomide, preferably teriflunomide, or a pharmaceutically acceptable salt thereof.

Suitable pharmaceutically acceptable salts of the DHODH inhibitor include both acid addition salts and base addition salts of said DHODH inhibitor. Examples of acid addition salts include, without limiting, the mesylate salt, the maleate salt, the fumarate salt, the tartrate salt, the hydrochloride salt, the hydrobromide salt, the esylate salt, the p-toluenesulfonate salt, the benzenesulfonate salt, the benzoate salt, the acetate salt, the phosphate salt, the sulfate salt, the citrate salt, the carbonate salt, and the succinate salt. Non-limiting examples of base addition salts include metal salts such as alkali metal salts, e.g., lithium, sodium or potassium salts, and alkaline earth metal salts, e.g., calcium or magnesium salts; and salts of ammonium ($NH_4^+$) or an organic cation derived from an amine of the formula $R_4N^+$, wherein each one of the Rs independently is H, $C_1$-$C_{22}$, preferably $C_1$-$C_6$, alkyl, such as methyl, ethyl, propyl, isopropyl, n-butyl, sec-butyl, isobutyl, tert-butyl, n-pentyl, 2,2-dimethylpropyl, n-hexyl, and the like, phenyl, or heteroaryl such as pyridyl, imidazolyl, pyrimidinyl, and the like, or two of the Rs together with the nitrogen atom to which they are attached form a 3-7 membered ring optionally containing a further heteroatom selected from N, S and O, such as pyrrolydine, piperidine and morpholine.

Additional pharmaceutically acceptable salts of the DHODH inhibitor include salts of a cationic lipid or a mixture of cationic lipids. Cationic lipids are often mixed with neutral lipids prior to use as delivery agents. Neutral lipids include, but are not limited to, lecithins; phosphatidylethanolamine; diacyl phosphatidylethanolamines such as dioleoyl phosphatidylethanolamine, dipalmitoyl phosphatidylethanolamine, palmitoyloleoyl phosphatidylethanolamine and distearoyl phosphatidylethanolamine; phosphatidylcholine; diacyl phosphatidylcholines such as dioleoyl phosphatidylcholine, dipalmitoyl phosphatidylcholine, palmitoyloleoyl phosphatidylcholine and distearoyl phosphatidylcholine; phosphatidylglycerol; diacyl phosphatidylglycerols such as dioleoyl phosphatidylglycerol, dipalmitoyl phosphatidylglycerol and distearoyl phosphatidylglycerol; phosphatidylserine; diacyl phosphatidylserines such as dioleoyl- or dipalmitoyl phosphatidylserine; and diphosphatidylglycerols; fatty acid esters; glycerol esters; sphingolipids; cardiolipin; cerebrosides; ceramides; and mixtures thereof. Neutral lipids also include cholesterol and other 3β hydroxy-sterols.

Examples of cationic lipid compounds include, without limiting, Lipofectin® (Life Technologies, Burlington, Ontario) (1:1 (w/w) formulation of the cationic lipid N-[1-(2,3-dioleyloxy)propyl]-N,N,N-trimethylammonium chloride and dioleoylphosphatidyl-ethanolamine); Lipofectamine™ (Life Technologies, Burlington, Ontario) (3:1 (w/w) formulation of polycationic lipid 2,3-dioleyloxy-N-[2(spermine-carboxamido)ethyl]-N,N-dimethyl-1-propan-amin-iumtrifluoroacetate and dioleoylphosphatidyl-ethanolamine), Lipofectamine Plus (Life Technologies, Burlington, Ontario) (Lipofectamine and Plus reagent), Lipofectamine 2000 (Life Technologies, Burlington, Ontario) (Cationic lipid), Effectene (Qiagen, Mississauga, Ontario) (Non liposomal lipid formulation), Metafectene (Biontex, Munich, Germany) (Polycationic lipid), Eu-fectins (Promega Biosciences, San Luis Obispo, Calif.) (ethanolic cationic lipids numbers 1 through 12: $C_{52}H_{106}N_6O_4.4 CF_3CO_2H$, $C_{88}H_{178}N_8O_4S_2.4 CF_3CO_2H$, $C_{40}H_{84}NO_3P.CF_3CO_2H$, $C_{50}H_{103}N_7O_3.4CF_3CO_2H$, $C_{55}H_{116}N_8O_2.6CF_3CO_2H$, $C_{49}H_{102}N_6O_3.4CF_3CO_2H$, $C_{44}H_{89}N_5O_3.2CF_3CO_2H$, $C_{100}H_{206}N_{12}O_4S_2.8CF_3CO_2H$, $C_{162}H_{330}N_{22}O_9.13CF_3CO_2H$, $C_{43}H_{88}N_4O_2.2CF_3CO_2H$, $C_{43}H_{88}N_4O_3.2CF_3CO_2H$, $C_{41}H_{78}NO_8P$); Cytofectene (Bio-Rad, Hercules, Calif.) (mixture of a cationic lipid and a neutral lipid), GenePORTER® (Gene Therapy Systems, San Diego, Calif.) (formulation of a neutral lipid (Dope) and a cationic lipid) and FuGENE 6 (Roche Molecular Biochemicals, Indianapolis, Ind.) (Multi-component lipid based non-liposomal reagent).

Pharmaceutically acceptable salts of the DHODH inhibitor may be formed by conventional means, e.g., by reacting a free base form of the DHODH inhibitor with one or more equivalents of the appropriate acid in a solvent or medium in which the salt is insoluble, or in a solvent such as water which is removed in vacuo or by freeze drying, or by exchanging the anion/cation of an existing salt for another anion/cation on a suitable ion exchange resin.

According to the method disclosed herein, the active agent capable of reducing DHODH enzyme activity in the CNS is administered either alone or together with a pyrimidine nucleobase or an intermediate in the de novo synthesis thereof.

The term "pyrimidine nucleobase" as used herein refers to any of the three types of nucleobases that are pyrimidine derivatives, i.e., uracil (pyrimidine-2,4(1H,3H)-dione; 2-oxy-4-oxy pyrimidine), cytosine (4-aminopyrimidin-2(1H)-one; 4-amino-1H-pyrimidine-2-one), and thymine (5-methylpyrimidine-2,4(1H,3H)-dione; 5-methyluracil).

The terms "de-novo pyrimidine synthesis" and "de novo pyrimidine nucleotide biosynthesis", used herein interchangeably, refer to the "orotate pathway", which is defined as the formation of uridine monophosphate (UMP) from carbamoyl phosphate (CP). The initial reaction in the orotate pathway catalyzed by CP synthetase is the formation of CP by combination of carbonate, adenosine triphosphate (ATP) and an amino group from glutamine Three additional reactions are necessary to form the pyrimidine ring from CP. The phosphoribosyl group of phosphoribosyl pyrophosphate is added to the pyrimidine base, orotate, forming orotidine 5'-monophosphate that is then decarboxylated to make UMP, the first pyrimidine nucleotide. UMP is subsequently phosphorylated to uridine diphosphate (UDP) and uridine triphosphate (UTP). The transfer of an amino group from glutamine to UTP by cytidine triphosphate (CTP) synthetase leads to the synthesis of CTP. UMP is also a precursor for the synthesis of cytidine monophosphate (CMP) and deoxythymidine monophosphate (dTMP).

In certain embodiments, the intermediate in the de novo synthesis of pyrimidine nucleobases is uridine, UMP, cytidine, CMP, deoxythymidine, or dTMP. In particular such embodiments, said intermediate is uridine or UMP.

In certain embodiments, the method of the present invention comprises administering to said subject a combination of agents, i.e., (i) a therapeutically effective amount of said active agent being capable of reducing DHODH enzyme activity in the CNS, e.g., a DHODH inhibitor or a pharmaceutically acceptable salt thereof, together with (ii) said pyrimidine nucleobase or intermediate in the de novo synthesis thereof, wherein each one of said agents is as defined in any one of the embodiments above. In particular such embodiments, said method comprises administering therapeutically effective amounts of leflunomide or teriflunomide, preferably teriflunomide, or a pharmaceutically acceptable salt thereof, together with uridine, UMP, cytidine, CMP, deoxythymidine, or dTMP, preferably UMP. According to the method of the invention, these two agents can be administered via the same or different administration routes, as well as concomitantly or subsequently at any order. In a particular embodiment, the two agents are administered from a sole pharmaceutical composition.

In other embodiments, the method of the present invention comprises administering to said subject a therapeutically effective amount of solely said active agent being capable of reducing DHODH enzyme activity in the CNS (i.e., without said pyrimidine nucleobase or intermediate in the de novo synthesis thereof), as defined in any one of the embodiments above, e.g., a DHODH inhibitor or a pharmaceutically acceptable salt thereof, wherein said subject does not suffer from multiple sclerosis. In particular such embodiments, the active agent administered is leflunomide or teriflunomide, preferably teriflunomide, or a pharmaceutically acceptable salt thereof.

In certain embodiments, the method of the invention, as defined in any one of the embodiments above, is utilized for treating or delaying onset of a neurodegenerative disease or disorder associated with elevated cortico-hippocampal activity. Examples of such neurodegenerative disease or disorder include, without limiting, epilepsy such as TLE or Dravet syndrome, also known as Severe Myoclonic Epilepsy of Infancy (SMEI); mild-cognitive impairments (MCI); or Alzheimer's disease, both sporadic and genetic. In particular such embodiments, the neurodegenerative disease or disorder treated according to said method is epilepsy, and said method is in fact aimed at preventing sudden unexplained death in epilepsy (SUDEP) of the subject treated.

In other embodiments, the subject treated by the method of the invention is at genetic risk for Alzheimer's disease, e.g., a subject carrying apolipoprotein E (APOE)-ε4, and said method, as defined in any one of the embodiments above, is aimed at preventing or delaying onset of Alzheimer's disease in said subject.

The term "subject" as used herein refers to a mammal that is either a human (herein also referred to as "individual") or a non-human animal.

The term "treating" as used herein with respect to a disease or disorder associated with cortico-hippocampal hyperactivity means administering an active agent capable of reducing DHODH enzyme activity in the CNS, e.g., teriflunomide or a pharmaceutically acceptable salt thereof, optionally together with a pyrimidine nucleobase or an intermediate in the de novo synthesis thereof, e.g., uridine or UMP, after the onset of at least one pathological phenotype manifested by said disease or disorder in order to treat, reduce or attenuate said pathological phenotype, and/or slow down the progression of said disease or disorder, i.e., prevent the appearance, or delay the onset, of other pathological phenotypes associated with said disease or disorder. The terms "preventing" and "delaying the onset" as used herein with respect to said disease or disorder mean administering said active agent, optionally together with said pyrimidine nucleobase or intermediate in the de novo synthesis thereof, to a subject either diagnosed as suffering from an elevated cortico-hippocampal activity or being at genetic risk for developing a disease or disorder associated with elevated cortico-hippocampal activity, prior to the onset of at least one pathological phenotype manifested by said disease or disorder, in order to prevent the appearance, or delay the onset, of said disease or disorder.

The term "therapeutically effective amount" as used herein refers to the amount or dose of an active agent as defined above, e.g., teriflunomide or a pharmaceutically acceptable salt thereof, that is useful to treat, attenuate, prevent, or delay the onset of at least one pathological phenotype manifested by a disease or disorder associated with elevated cortico-hippocampal activity.

According to the method of the present invention, each one of the active agent and the pyrimidine nucleobase or intermediate in the de novo synthesis thereof, as defined in any one of the embodiments above, may be administered independently by any suitable administration route, e.g., intravenously, intraarterially, intrathecally, intrapleurally, intratracheally, intraperitoneally, intramuscularly, subcutaneously, topically, orally, or by inhalation. In other words, in case said active agent is administered together with said pyrimidine nucleobase or intermediate in the de novo synthesis thereof, both agents may be delivered by the same administration route, from either a sole pharmaceutical composition or two different pharmaceutical compositions, or by different administration routes.

In certain embodiments, the method of the present invention is aimed at treating a neurodegenerative disease or disorder such as epilepsy (e.g., TLE or Dravet syndrome), MCI or AD, and comprises intrathecal administration of an active agent, as defined in any one of the embodiments above, wherein a pyrimidine nucleobase or an intermediate in the de novo synthesis thereof is optionally administered together with said active agent, by any suitable administration route, but preferably by intrathecal administration as well. In particular such embodiments, the active agent is teriflunomide or a pharmaceutically acceptable salt thereof that is delivered intrathecally, optionally together with a pyrimidine nucleobase or an intermediate in the de novo synthesis thereof.

In a particular embodiment, the present invention thus relates to a method for treatment of a neurodegenerative disease or disorder such as epilepsy, MCI or AD, or for preventing or delaying onset of AD in a subject being at genetic risk for AD, said method comprising intrathecally administering teriflunomide or a pharmaceutically acceptable salt thereof, either alone or in combination with a pyrimidine nucleobase or an intermediate in the de novo synthesis thereof. In a specific such embodiment, teriflunomide or a pharmaceutically acceptable salt thereof is administered alone.

In another aspect, the present invention relates to an active agent capable of reducing DHODH enzyme activity in the CNS for use, optionally in combination with a pyrimidine nucleobase or an intermediate in the de novo synthesis thereof, in preventing, delaying onset of, or treating a disease or disorder associated with cortico-hippocampal hyperactivity. In certain embodiments, said active agent comprises a nucleic acid molecule that reduces the gene expression level of DHODH enzyme, as defined above. In other embodiments, said active agent is a small molecule capable of reducing DHODH enzyme activity in the CNS, such as leflunomide, teriflunomide, brequinar, DD264, or a pharmaceutically acceptable salt thereof, e.g., teriflunomide or a pharmaceutically acceptable salt thereof. Particular pyrimidine nucleobases or intermediates in the de novo synthesis thereof include, without being limited to, uridine, UMP, cytidine, CMP, deoxythymidine, and dTMP. Examples of diseases or disorders associated with cortico-hippocampal hyperactivity include, without limiting, neurodegenerative diseases or disorders such as epilepsy, e.g., TLE, or Dravet syndrome; MCI; or Alzheimer's disease.

It yet another aspect, the present invention provides a pharmaceutical composition for preventing, delaying onset of, or treating a disease or disorder associated with cortico-hippocampal hyperactivity, said composition comprising an active agent capable of reducing DHODH enzyme activity in the CNS as defined in any one of the embodiments above, and optionally a pyrimidine nucleobase or an intermediate in the de novo synthesis thereof as defined in any one of the embodiments above. Particular such compositions comprise said active agent alone, while other compositions comprise both said active agent and said pyrimidine nucleobase or intermediate in the de novo synthesis thereof. In certain embodiments, the active agent comprised within the composition disclosed herein is a nucleic acid molecule that reduces the gene expression level of DHODH enzyme, as defined above. In other embodiments, said active agent is a small molecule capable of reducing DHODH enzyme activity in the CNS, such as leflunomide, teriflunomide, brequinar, DD264, or a pharmaceutically acceptable salt thereof, e.g., teriflunomide or a pharmaceutically acceptable salt thereof. Particular pyrimidine nucleobases or intermediates in the de novo synthesis thereof, optionally comprised within the composition disclosed herein, include, without being limited to, uridine, UMP, cytidine, CMP, deoxythymidine, and dTMP. Examples of diseases or disorders associated with cortico-hippocampal hyperactivity include, without limiting, neurodegenerative diseases or disorders such as epilepsy, e.g., TLE, or Dravet syndrome; MCI; or Alzheimer's disease.

In still another aspect, the present invention provides a pharmaceutical composition comprising an active agent capable of reducing DHODH enzyme activity in the CNS as defined in any one of the embodiments above, and a pyrimidine nucleobase or an intermediate in the de novo synthesis thereof as defined in any one of the embodiments above. In certain embodiments, the active agent comprised within the composition disclosed herein is a nucleic acid molecule that reduces the gene expression level of DHODH enzyme, as defined above. In other embodiments, said active agent is a small molecule capable of reducing DHODH enzyme activity in the CNS, such as leflunomide, teriflunomide, brequinar, DD264, or a pharmaceutically acceptable salt thereof, e.g., teriflunomide or a pharmaceutically acceptable salt thereof. Examples of pyrimidine nucleobase or intermediates in the de novo synthesis thereof include, e.g., uridine, UMP, cytidine, CMP, deoxythymidine, and dTMP.

Pharmaceutical compositions according to the present invention may be prepared by conventional techniques, e.g., as described in Remington: The Science and Practice of Pharmacy, 19th Ed., 1995. The compositions can be prepared, e.g., by uniformly and intimately bringing the active ingredient(s), i.e., said active agent capable of reducing DHODH enzyme activity in the CNS, said pyrimidine nucleobase or intermediate in the de novo synthesis thereof, or both, into association with a liquid carrier, a finely divided solid carrier, or both, and then, if necessary, shaping the product into the desired formulation. The compositions may be in liquid, solid or semisolid form and may further include pharmaceutically acceptable fillers, carriers, diluents or adjuvants, and other inert ingredients and excipients. In one embodiment, the pharmaceutical composition of the present invention is formulated as nanoparticles.

The pharmaceutical compositions disclosed herein may be formulated for any suitable route of administration, e.g., for parenteral administration such as intravenous, intraarterial, intrathecal, intrapleural, intratracheal, intraperitoneal, intramuscular or subcutaneous administration, topical administration, oral or enteral administration, or for inhalation, and can be provided in a variety of dosages. Particular such compositions are formulated for intrathecal, intraperitoneal or intravenous administration, or for subcutaneous administration e.g. by an alzet pump implanted subcutaneously, but preferably for intrathecal administration. The dosage will depend on the state of the subject treated, and will be determined as deemed appropriate by the practitioner.

The pharmaceutical composition of the invention may be in the form of a sterile injectable aqueous or oleaginous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution, PEG, 2-hydroxypropyl-β-cyclodextrin (HPCD), Tween-80, and isotonic sodium chloride solution.

Pharmaceutical compositions according to the present invention, when formulated for administration route other than parenteral administration, may be in a form suitable for oral use, e.g., as tablets, troches, lozenges, aqueous, or oily suspensions, dispersible powders or granules, emulsions, hard or soft capsules, or syrups or elixirs.

Pharmaceutical compositions intended for oral administration may be formulated for immediate release, or alternatively to inhibit the release of the active agent in the stomach, i.e., delay the release of the active agent until at least a portion of the dosage form has traversed the stomach, e.g., to avoid the acidity of the gastric contents from hydrolyzing the active agent. Particular such compositions are those wherein the active agent is coated by a pH-dependent enteric-coating polymer. Examples of pH-dependent enteric-coating polymer include, without being limited to, Eudragit® S (poly(methacrylicacid, methylmethacrylate), 1:2), Eudragit® L 55 (poly (methacrylicacid, ethylacrylate), 1:1), Kollicoat® (poly(methacrylicacid, ethylacrylate), 1:1), hydroxypropyl methylcellulose phthalate (HPMCP), alginates, carboxymethylcellulose, and combinations thereof. The pH-dependent enteric-coating polymer may be present in the composition in an amount from about 10% to about 95% by weight of the entire composition.

Pharmaceutical compositions intended for oral administration may be prepared according to any method known in the art, and may further comprise one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents, e.g., magnesium stearate, stearic acid, or talc. The tablets may be either uncoated or coated utilizing known techniques to delay disintegration and absorption in the gastrointestinal tract and thereby provide a sustained action over a longer period. For example, a time delay material such as glyceryl monostearate or glyceryl distearate may be employed. They may also be coated using the techniques described in the U.S. Pat. Nos. 4,256,108, 4,166,452 and 4,265,874 to form osmotic therapeutic tablets for control release. The pharmaceutical composition of the invention may also be in the form of oil-in-water emulsion.

Oral pharmaceutical compositions may be formulated for immediate release, as well as for controlled release, i.e., extended-, sustained-, or delayed-release, of the active agent. Such compositions may be formulated as controlled-release matrix, e.g., as controlled-release matrix tablets in which the release of a soluble active agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity. In other configurations, the compositions comprise the active agent formulated for controlled release in microencapsulated dosage form, in which small droplets of the active agent are surrounded by a coating or a membrane to form particles in the range of a few micrometers to a few millimeters.

Another contemplated formulation is depot systems, based on biodegradable polymers, wherein as the polymer degrades, the active ingredient is slowly released. The most common class of biodegradable polymers is the hydrolytically labile polyesters prepared from lactic acid, glycolic acid, or combinations of these two molecules. Polymers prepared from these individual monomers include poly (D,L-lactide) (PLA), poly (glycolide) (PGA), and the copolymer poly (D,L-lactide-co-glycolide) (PLG).

Pharmaceutical compositions according to the present invention, when formulated for inhalation, may be administered utilizing any suitable device known in the art, such as metered dose inhalers, liquid nebulizers, dry powder inhalers, sprayers, thermal vaporizers, electrohydrodynamic aerosolizers, and the like.

In a further aspect, the present invention provides a kit comprising: (i) a first pharmaceutical composition comprising an active agent capable of reducing DHODH enzyme activity in the CNS as defined in any one of the embodiments above; (ii) a second pharmaceutical composition comprising a pyrimidine nucleobase or an intermediate in the de novo synthesis thereof as defined in any one of the embodiments above; and optionally (iii) instructions for co-administration of said pharmaceutical compositions for preventing, delaying onset of, or treating a disease or disorder associated with cortico-hippocampal hyperactivity. Examples of disease or disorder associated with cortico-hippocampal hyperactivity include, without limiting, neurodegenerative diseases or disorders such as epilepsy, e.g., TLE, or Dravet syndrome; MCI; or Alzheimer's disease.

The active agent comprised within the first composition of the kit may be any agent capable of reducing DHODH enzyme activity in the CNS, e.g., an active agent comprising a nucleic acid molecule that reduces the gene expression level of DHODH enzyme; or a small molecule capable of reducing DHODH enzyme activity in the CNS, such as leflunomide, teriflunomide, brequinar, DD264, or a pharmaceutically acceptable salt thereof, e.g., teriflunomide or a pharmaceutically acceptable salt thereof. Examples of pyrimidine nucleobases or intermediates in the de novo synthesis thereof, which may be comprised within the second composition, include uridine, UMP, cytidine, CMP, deoxythymidine, and dTMP. According to the present invention, the pharmaceutical compositions comprised within the kit disclosed herein may be formulated for the same or different administration route, and may be administered concomitantly or subsequently at any order. In particular embodiments, the first pharmaceutical composition and optionally the second pharmaceutical composition is(are) formulated for intrathecal administration.

Based on the experimental data shown herein, it is postulated that intrathecal administration of an active agent as referred to herein in general, and of teriflunomide in particular, is expected to be substantially more efficient in treating multiple sclerosis compared to other administration modes such as intravenously or intraperitoneally.

In yet a further aspect, the present invention thus relates to a method for treatment of multiple sclerosis in a subject in need thereof, said method comprising intrathecally administrating to said subject a therapeutically effective amount of an active agent capable of reducing DHODH enzyme activity in the CNS of said subject, as defined in any one of the embodiments above, e.g., teriflunomide or a pharmaceutically acceptable salt thereof.

In still a further aspect, the present invention relates to an active agent capable of reducing DHODH enzyme activity in the CNS, as defined in any one of the embodiments above, e.g., teriflunomide or a pharmaceutically acceptable salt thereof, for use in treatment of multiple sclerosis, wherein said active agent is formulated for intrathecal administration.

The invention will now be illustrated by the following non-limiting Examples.

EXAMPLES

Example 1. DHODH is a Potential Metabolic Target for Epilepsy and MCI

To search for novel, disease-transformative common targets for epilepsy, MCI and prodromal AD, a system-based approach for attenuation of hippocampal hyperactivity, more specifically the metabolic transformation algorithm (MTA) recently developed by the Ruppin lab (Yizhak et al., 2013), was used. The MTA is a generic genome scale metabolic modeling (GSMM) analysis approach for predicting genetic perturbations that are most likely to transform a given source metabolic state to a desired target one, which has been successfully applied to predict and experimentally validate two novel life-extending metabolic genes (Yizhak et al., 2013).

Applying the MTA to the analysis of human MCI and epilepsy pilocarpine rat model gene expression data, we conducted an in silico knockout screen of all human metabolic genes and ranked them according to their ability to transform a diseased metabolic state back to the corresponding healthy state. This analysis revealed the DHODH mitochondrial enzyme as the most significantly predicted common epilepsy and MCI target that may transform diseased metabolic state into a normal healthy state. DHODH is the fourth enzyme in the pyrimidine-de-novo synthesis, catalyzing the conversion of dihydroorotate to orotate and inhibiting the mETC irrespective of de-novo pyrimidine synthesis (Fang et al., 2013). Interestingly, both the DHODH inhibitor leflunomide and its active metabolite teriflunomide are used for the treatment of multiple sclerosis (Compston and Coles, 2008). It is assumed that DHODH inhibition targets rapidly proliferating cells such as T- and B-lymphocytes that rely on pyrimidine-de-novo synthesis and thus helps regulating the inflammatory response, but the exact mechanisms by which DHODH inhibition benefits multiple sclerosis patients is unclear (Bar-Or, 2014). Yet, whether DHODH inhibition directly regulates neuronal activity remains unknown.

Figure 1B:
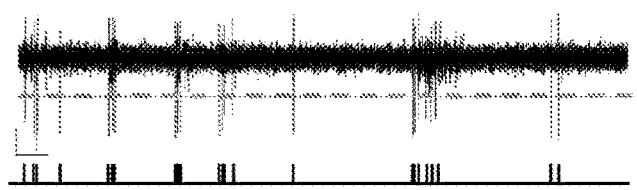
Figure 1C:
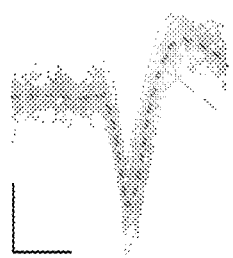
Figure 1D:
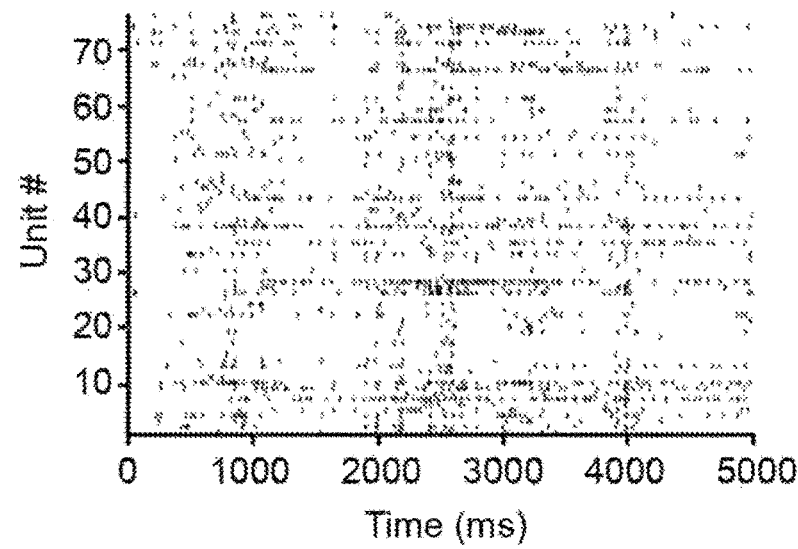
Figure 1E:
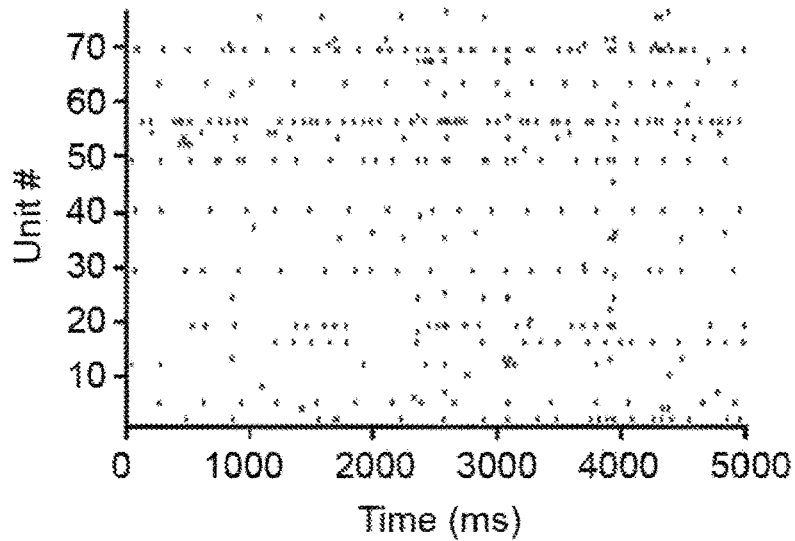
Figure 1F:
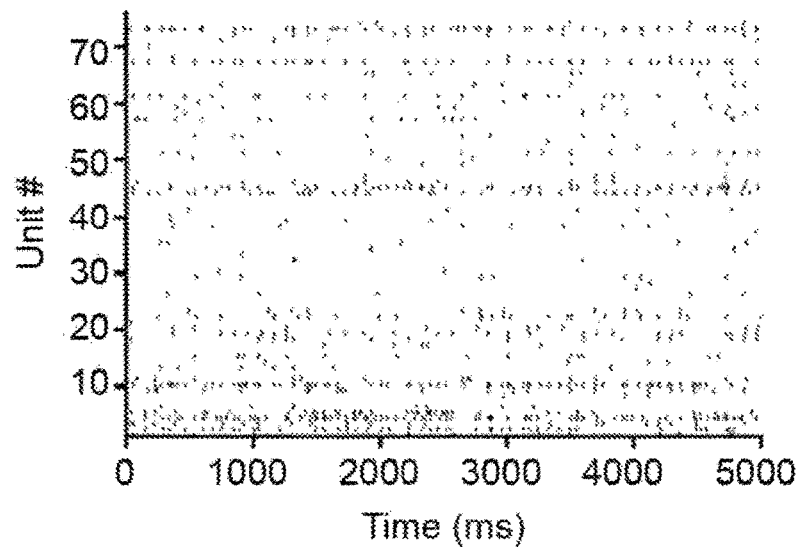

Example 2. DHODH Inhibition Induces a Stable Reduction of Mean Firing Rates in Hippocampal Networks In order to test how DHODH targeting affects neuronal activity, we examined the effect of the DHODH inhibitor teriflunomide on cultured hippocampal neurons grown on a multi-electrode chip (MEA) that allows a long-term monitoring of spiking activity from many neurons simultaneously (FIGS. 1A-1C). As found, addition of 50 μM teriflunomide resulted in fast and stark decrease in neuronal mean firing rate (MFR, FIGS. 1D-1F, 1H), which was reduced from 3.95±0.27 Hz during baseline to 1.58±0.17 Hz after 4 h of teriflunomide application. Interestingly, the lower MFR induced by teriflunomide was stable for 14 hr following teriflunomide application (FIGS. 1G-1H), indicating that neuronal homeostatic mechanisms are unable to compensate DHODH-induced inhibition of firing frequency and that changes induced by teriflunomide application are stable.

Figure 1G:
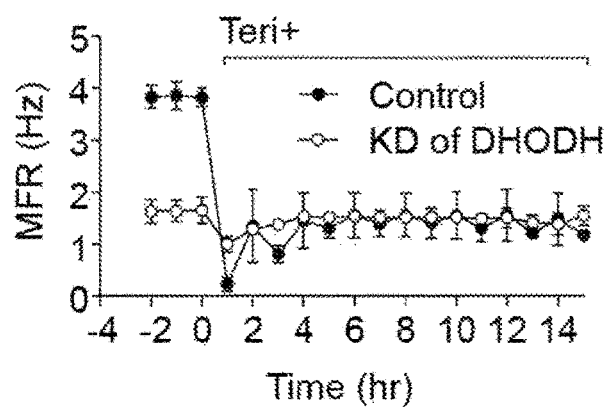
Figure 1H:
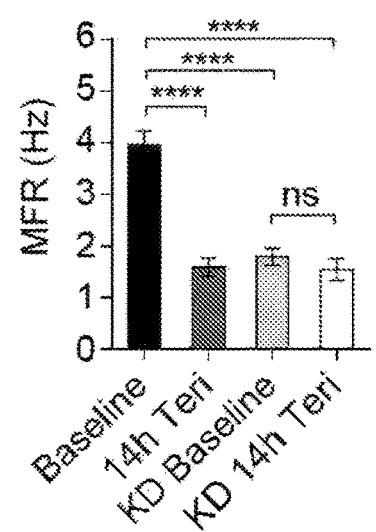

In order to test the specificity of teriflunomide effect on firing rate, we used a lentiviral-based shRNA delivery system (shDHODH; TRCN0000294665, Sigma Aldrich) to knockdown DHODH expression in hippocampal cultures. As found, reduction in DHODH mRNA level by ~80% resulted in a lower basal MFR (1.78±0.17 Hz, FIGS. 1G-1H); however, application of teriflunomide in shDHODH-infected cultures did not produce long-term changes in MFR (FIG. 1G). These results indicate that teriflunomide specifically inhibits DHODH to induce a stable reduction in the MFR in hippocampal neurons, and therefore support its potential anti-epileptic function.

Figure 2A:
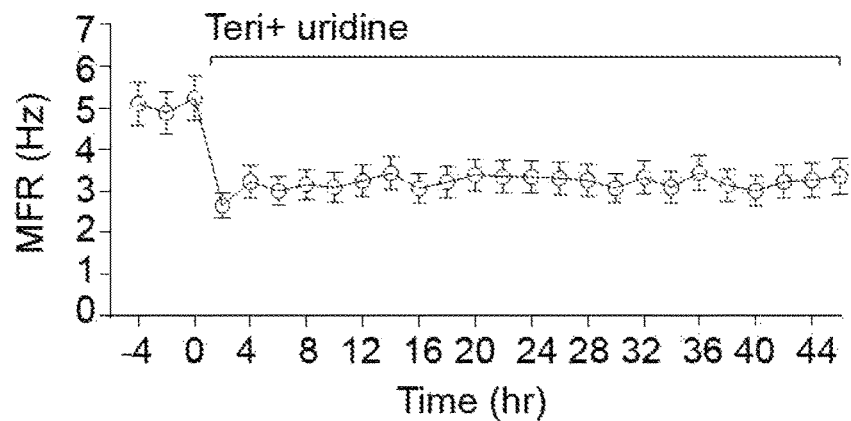
FIGS. 2A-2B show that teriflunomide-induced reduction in firing rate does not depend on de novo pyrimidine synthesis. (2A) Application of 100 μM uridine with 50 μM teriflunomide did not occlude the effect of teriflunomide on MFR; (2B) Reduction in MFR was significant (105 single units, ****p<0.0001, using Wilcoxon non-parametric t-test).
Figure 2B:
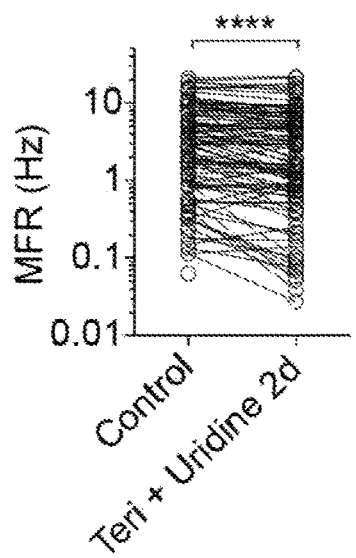

Example 3. DHODH-Mediated Inhibition of Firing Rates is not Dependent on De Novo Pyrimidine Synthesis In order to test whether the change in MFR resulting from DHODH inhibition is induced by the reduction of available uridine (a precursor of pyrimidines) or results from a change in the mitochondrial function, we co-applied 100 μM uridine mono-phosphate with teriflunomide in MEA recordings. As found, addition of uridine did not occlude the reduction in MFR induced by teriflunomide at a timescale of 2 days (FIG. 2), indicating that lack of uridine is not the factor that leads to long-term reduction in the MFR; and suggesting that DHODH inhibition triggers a long-term reduction in the MFR due to its direct inhibition of mitochondrial functions rather than de-novo pyrimidine synthesis.

Example 4. DHODH Inhibition Induces a Reduction in Intrinsic Excitability

Figure 3A:
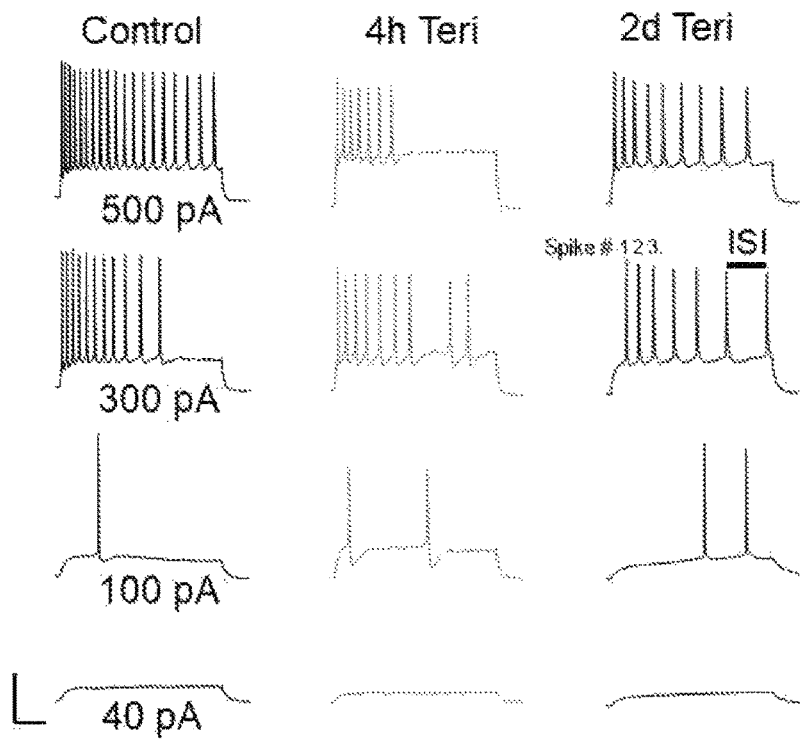
FIGS. 3A-3E show that DHODH inhibition reduces intrinsic excitability. (3A) Representative traces of voltage responses evoked by 20 pA step of current injections after control, 4 hr and 2 days teriflunomide incubation, elicited from −60 mv holding potential (scale bars: 40 mV, 100 ms); (3B-3C) Frequency-current (F-I) relationship after control, 4 hr and 2 days teriflunomide incubation. Both 4 hr and 2d teriflunomide incubation show a reduction in maximal firing rate (control, n=20; 4 hr, n=15; 2 days, n=8). (3D) A series of sub-threshold current injections was given (see insert) and voltage-currant relationship was plotted and fitted with linear regression; (3E) Input resistance ($R_{in}$) calculated from slope of voltage current curves in 3D showed no change following teriflunomide incubation. One-way ANOVA was used, *p<0.05, **p<0.001.
Figure 3B:
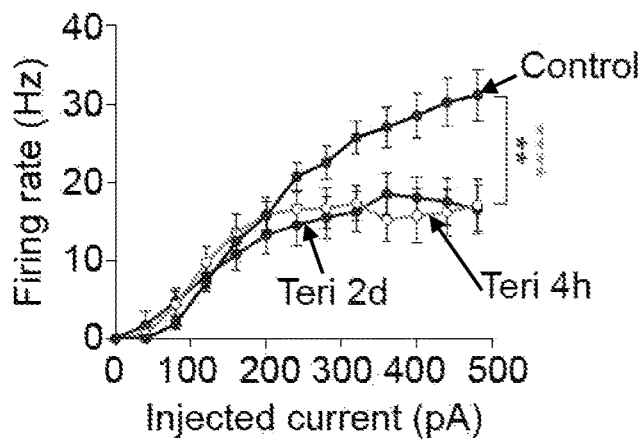
Figure 3C:
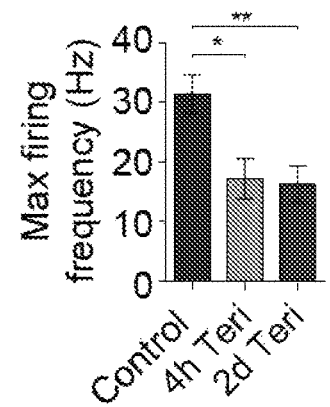
Figure 3D:
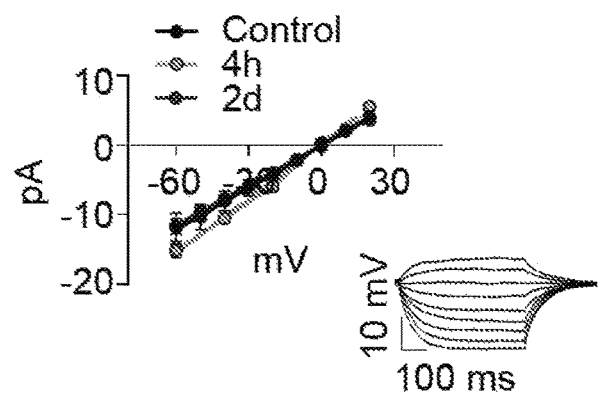
Figure 3E:
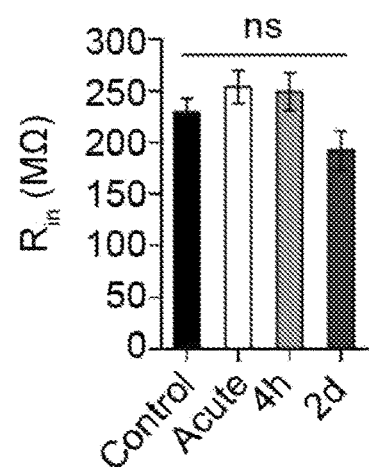

Modulation of intrinsic excitability is an important facet of neuronal adaptation. In this experiment we elicited action potentials (APs) in response to increasing somatic current injections ranging from 0 to +500 pA (F-I curves) in the presence of postsynaptic receptor blockers (FIGS. 3A-3B). As found, teriflunomide induced a reduction in the maximal firing frequency from 31.4±2.29 Hz to 17.2±3.34 after 4 hr of incubation, and to 16.25±3.06 Hz after 2 days of incubation (FIGS. 3B-3C). Input resistance was not affected by teriflunomide application (FIGS. 3D-3E). These results indicate that DHODH inhibition reduces intrinsic neuronal excitability, and that this change is resistant to homeostatic adaptations and remains stable for 2 days.

Figure 4A:
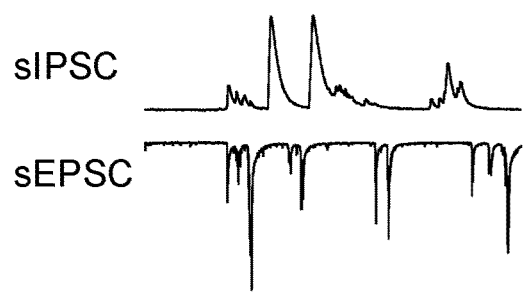
FIGS. 4A-4D show that DHODH inhibition triggers an increase in inhibition-excitation (I/E) ratio. (4A) Representative traces of sEPSCs (−65 mV holding potential, bottom) and sIPSCs (+10 mV holding potential, top). (4B) Mean integrated excitatory conductance ($G_E$) in control (n=19), 4 hr (n=13) and 2 days (n=19) teriflunomide application. Excitatory conductance remained lower for 2 days following exposure to teriflunomide. (4C) Excitatory conductance ($G_I$) shows no significant change after teriflunomide incubation. (4D) The ratio between $G_I$ and $G_E$ per neuron was elevated and remained high over the 2-day incubation period. Error bars represent SEM. (p<0.05, p<0.001, *p<0.0001; Tukey's multiple comparison test).
Figure 4B:
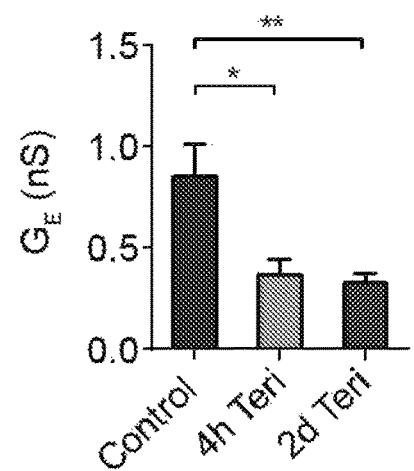
Figure 4C:
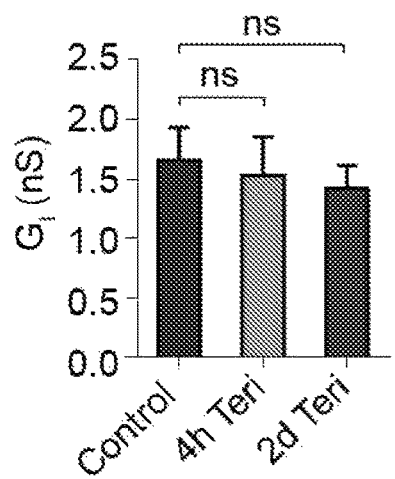

Example 5. DHODH Inhibition Induces an Increase in the Inhibition-Excitation Ratio The inhibition-excitation (I/E) ratio constitutes an important factor in firing rate homeostasis, and in pathology of epilepsy. To assess the effects of DHODH inhibition on the I/E ratio, the spontaneous excitatory and inhibitory postsynaptic currents (sEPSCs, sIPSCs, respectively) were isolated at the same cell based on the reversal potentials of α-amino-3-hydroxy-5-methyl-4-isoxazolepropionic acid receptor (AMPAR)-mediated excitatory and $GABA_AR$-mediated inhibitory currents, and the integrated excitatory (FIG. 4A) and inhibitory conductance's ($G_E$, $G_I$, respectively) were calculated (FIGS. 4B-4D).

Figure 4D:
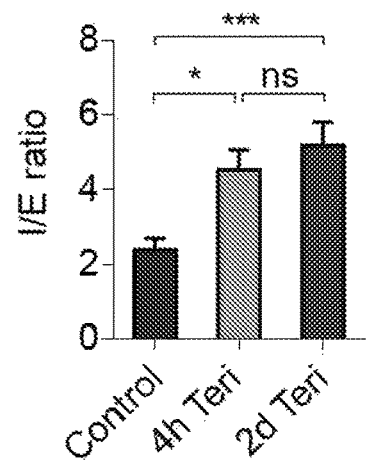
Figure 5A:
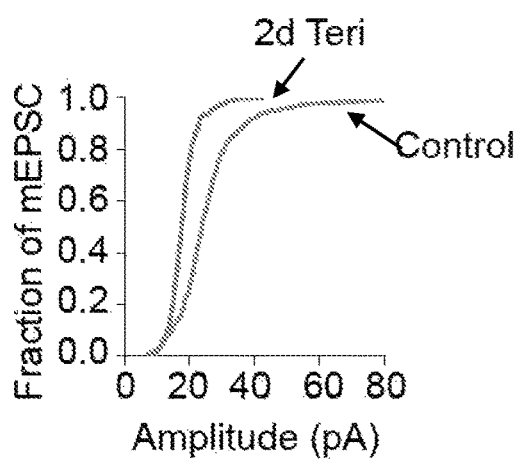
FIGS. 5A-5D show that chronic DHODH inhibition triggers a decrease in mEPSC amplitude. (5A) Cumulative histograms of mEPSC amplitudes in control (n=14) and following 2 days teriflunomide incubation (n=16). (5B) Summary of data in 5A. Mean mEPSC amplitude is significantly reduced by 26% (p=0.0001) after 2 days teriflunomide incubation. (5C) Cumulative histogram of mEPSC inter-event intervals showing a gradual shift to bigger values from control to 2 days teriflunomide incubation (the same experiments as in A-B). (5D) Summary of data in 5C. mEPSC frequency is not significantly affected (p=0.08). ***p<0.001; unpaired t-test. Error bars represent SEM.
Figure 5B:
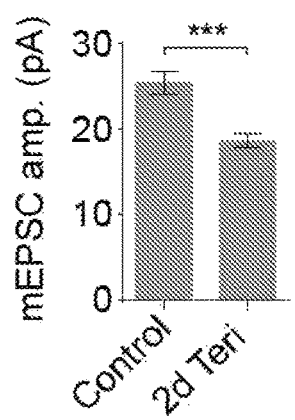
Figure 5C:
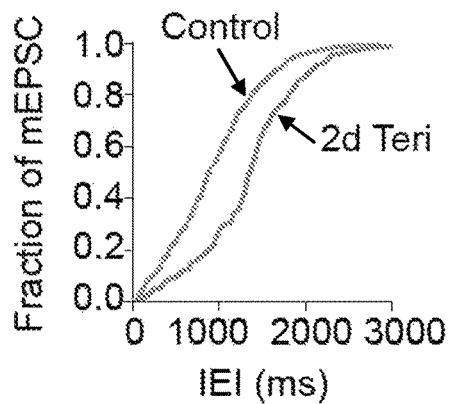
Figure 5D:
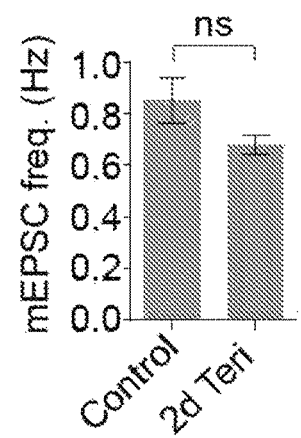
Figure 6A:
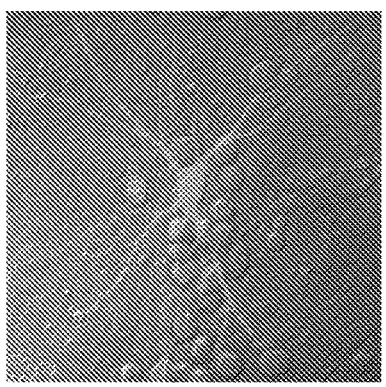
FIGS. 6A-6D show that DHODH inhibition induces an increase in intrinsic excitability of fast-spiking parvalbumin-expressing neurons (PV neurons). (6A) Example of PV neuron expressing m-Cherry. (6B) Representative traces of voltage responses evoked by 2500 pA current step in control (top) and 2 days teriflunomide incubation (bottom). (6C) F-I relationship shows an increase in firing frequency of PV cells after 2d teriflunomide incubation (n=19-21). Two-way ANOVA with Sidak's multiple comparisons. p<0.0001. (6D) Average MFR at 2500 pA (n=19-21, p=0.011, unpaired t-test).
Figure 6B:
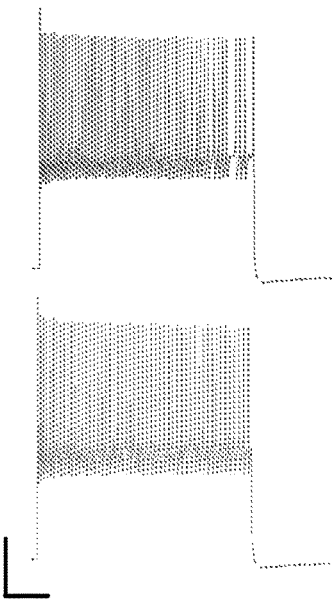
Figure 6C:
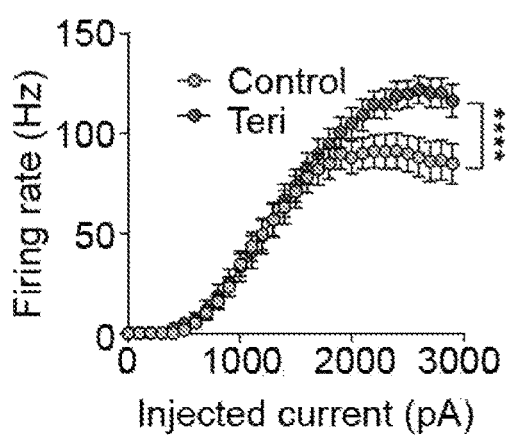
Figure 6D:
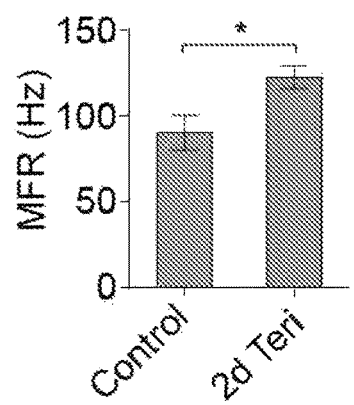

The results show a dramatic decrease in average $G_E$ after 4 hr of teriflunomide incubation, which was stable during 2 days of incubation (FIG. 4B) and resulted in a significant and stable increase in I/E ratio (FIG. 4D). This decrease was selective to the excitatory synaptic drive, as $G_I$ showed no significant reduction after either 4 hr or 2 days of incubation (FIG. 4C). These results indicate that the reduction in the MFR induced by teriflunomide is correlated with a change in the network balance between excitation and inhibition, and that DHODH inhibition and downstream mitochondrial signaling may have a differential effect on excitatory and inhibitory neurons.

Example 6. DHODH Inhibition Induces a Decrease in Excitatory Quantal Amplitude

In this experiment we tested whether DHODH inhibition affects excitatory quantal events, by recording mEPSCs from hippocampal neurons under control conditions and 2 days following teriflunomide application (FIG. 5). As found, chronic teriflunomide incubation triggered a significant decrease of ~26% in mEPSC amplitude (FIGS. 5A-5B). In addition, a tendency towards reduction in mEPSC frequency was observed, but did not reach statistical significance (FIGS. 5C-5D, p=0.08). These data suggest that chronic DHODH inhibition triggers robust inhibition of quantal excitatory synaptic transmission, likely due to reduction in the number/conductance of the postsynaptic AMPARs.

Example 7. DHODH Inhibition Induces an Increase in Excitability of Fast-Spiking PV Interneurons The fast spiking phenotype of parvalbumin-expressing neurons (PV cells) exerts high metabolic demands, and PV cells express high density of mitochondria to support this function (Gulyaz et al., 2006). These facts make PV cells extremely sensitive to metabolic stress (Whittaker et al., 2011). In order to test whether the increase in the I/E ratio results from the differential teriflunomide effect on excitatory and inhibitory neurons, we decided to measure intrinsic excitability in fast-spiking PV cells. To specifically examine PV cell properties, we used cultures from mice that express Cre-recombinase under a PV promotor, and infected them with a double-floxed AAV virus to produce targeted expression of the fluorescent tag m-Cherry (FIG. 6). PV cells were identified by their non-accommodating fast-spiking phenotype.

As surprisingly found, teriflunomide triggered an increase in maximal firing rate of PV cells from 83.50±11.04 to 110.9±7.22 after 2 days of teriflunomide incubation, indicating that the metabolic regulation of inhibitory PV cells differs from that of excitatory cells, and that this differential regulation most probably contributes to the increase in the I/E ratio and the reduction in MFR.

Example 8. DHODH Inhibition does not Impair Neuronal Homeostatic System

Figure 7A:
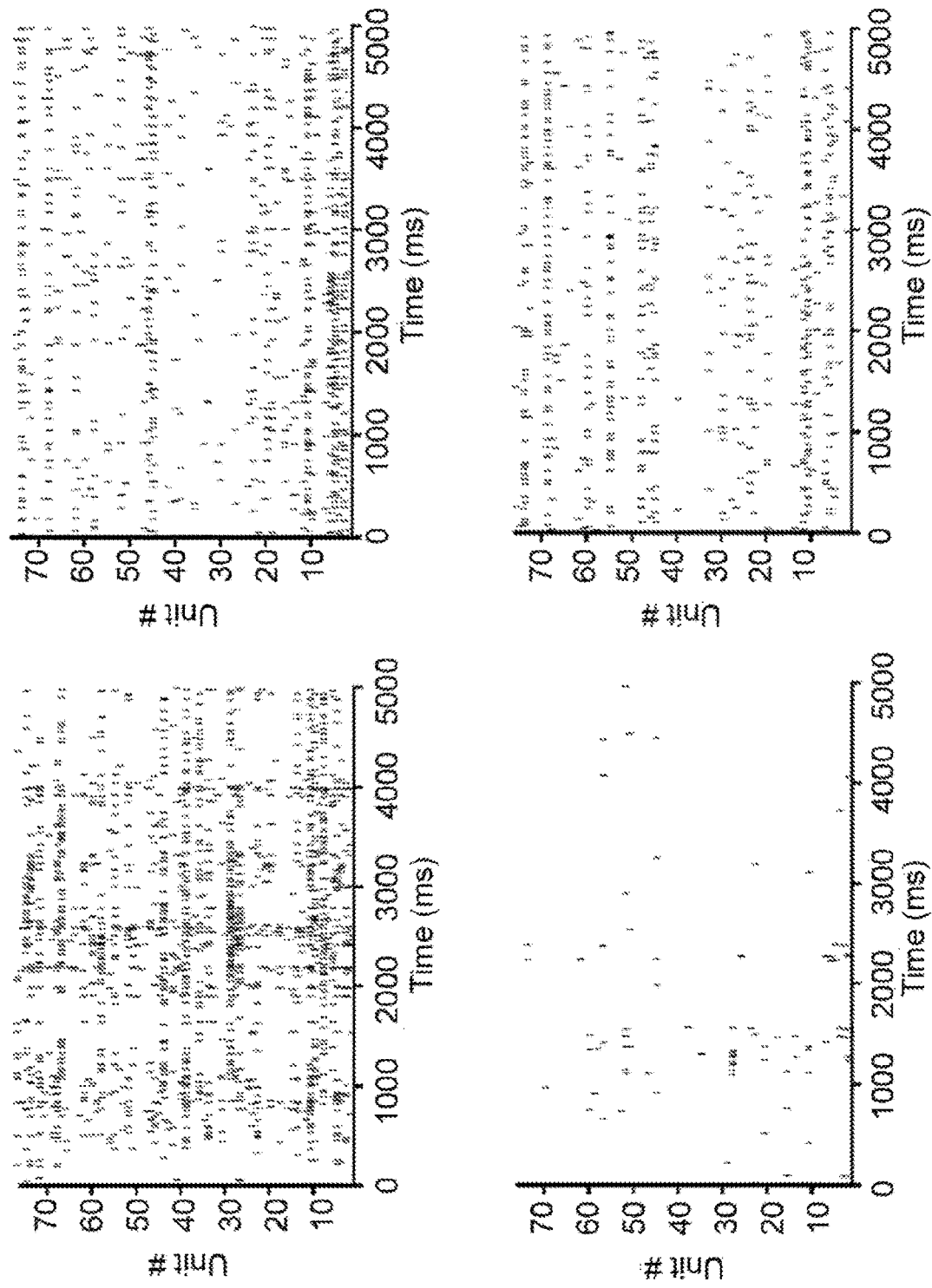
FIGS. 7A-7C show that DHODH inhibition lowers the neuronal MFR set point. (7A) Raster plots of activity at baseline (top, left), after overnight incubation with teriflunomide (top, right), acute application of 10 μM baclofen (bottom, left) and 48 h after baclofen application (bottom, right). (7B) Example of MFR of culture treated with 50 μM teriflunomide overnight, then 10 μM baclofen was added. MFR was acutely reduced, but gradually compensated back to a stead state, but significantly lower than original baseline. (7C) Average MFR shows homeostatic correction towards a new set-point induced by teriflunomide incubation. n=140 units, 2 experiments. p<0.01, **p<0.0001 using 2-way ANOVA.
Figure 7B:
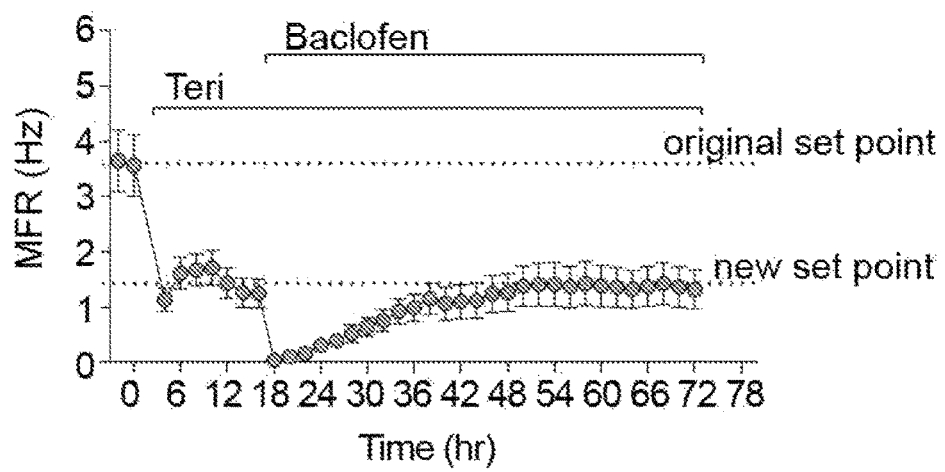
Figure 7C:
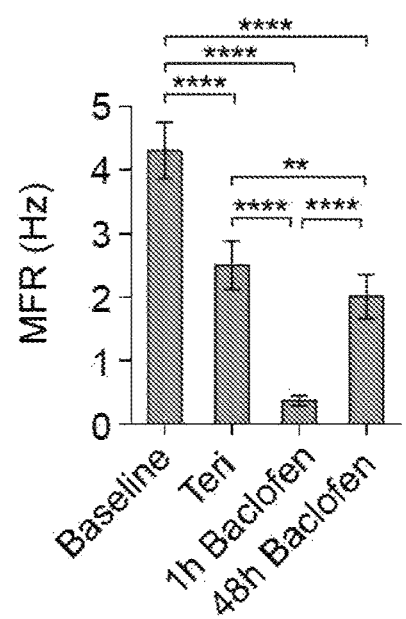

The stable reduction in MFR induced by teriflunomide could have been the result of either impairment of homeostatic compensation mechanisms, or a change in a firing set-point value. A perturbation of firing rate in vivo results in re-normalization to its set-point level 2 days following perturbation through homeostatic mechanisms (Hengen et al., 2013). Similarly, application of baclofen results in a profound inhibition of firing rate that returns to it baseline level after 2 days (Slomowitz et al., 2015). In order to determine the role DHODH inhibition in homeostatic process, we added 10 μM baclofen following 12 hr incubation with teriflunomide (FIG. 7).

As found, addition of baclofen in the presence of teriflunomide reduced MFR acutely from a new lower baseline value of 2.50±0.38 Hz to 0.3678±0.08 Hz. This reduction was gradually corrected over a 2-day period; however, the culture did not reach the original baseline value of 4.30±0.0.44 Hz. Instead, the MFR stabilized around a lower value of 2.00±0.35 Hz, closer to the one induced by teriflunomide incubation. These results suggest that homeostatic compensation mechanisms are still active under DHODH inhibition, yet are tuned to drive the steady-state of the network to a lower set-point level.

Figure 8:
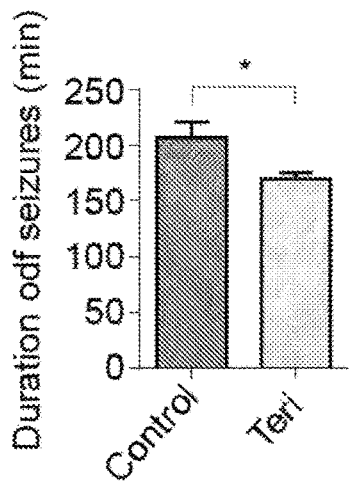
FIG. 8 shows that teriflunomide reduces behavioral seizure duration in pilocarpine model for TLE. Daily IP injections of 15 mg/kg teriflunomide (n=12) or vehicle (n=11) were performed for 3 days, and on the 3$^{rd}$ day status epilepticus was induced with SC injection of scopolamine 2 mg/kg, and 30 min later an IP injection of 330 mg/kg pilocarpine. *p<0.05, unpaired Student's t-test.

Example 9. DHODH Inhibition Reduces Behavioral Seizure Duration in Pilocarpine Model for TLE In order to determine the potential therapeutic benefit of DHODH inhibition for epilepsy treatment, we used the pilocarpine model of TLE, which is one of the most common mouse models that recapitulates many aspects of the human pathology. The pilocarpine model of TLE appears to be highly isomorphic with the human disease including induction of acute status epilepticus, and latent period followed by the appearance of spontaneous recurrent seizures, as well as the occurrence of widespread lesions in the CNS (Curia et al., 2008). These features make it highly suitable for testing the efficacy of antiepileptic drugs (Leite et al., 2002). We performed intraperitoneal (IP) daily injections of teriflunomide (15 mg/kg) or vehicle for 3 days, in 6-week-old male mice of C57 background. On the third day, mice were injected subcutaneously (SC) with 2 mg/kg scopolamine to prevent peripheral effects, and 30 min later with 330 mg/kg pilocarpine IP. As found, IP injections of teriflunomide significantly reduces behavioral seizure duration induced by pilocarpine (FIG. 8, p=0.0157). Because seizure duration correlates with hippocampal pathology in the pilocarpine model (Mazzuferi et al., 2012), these in vivo results emphasize the potential of DHODH inhibition as a therapeutic approach in the most common form of epilepsy.

Figure 9A:
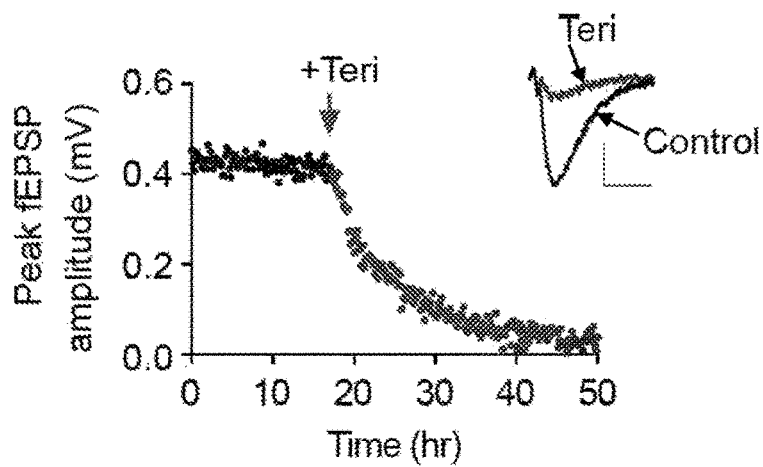
FIGS. 9A-9D show the effect of teriflunomide on CA3-CA1 basal synaptic transmission and short-term plasticity in acute hippocampal slices. (9A) Time-course of 50 μm teriflunomide effect on fEPSP amplitude. (9B) Teriflunomide reduced input-output relationship between the intensity of the fiber volley amplitude and the fEPSP slope (n=7, two-way ANOVA, p<0.0001). (9C) Representative recordings of fEPSP evoked by bursts (5 stimuli at 50 Hz) in acute hippocampal slices before and 30 min after application of teriflunomide. (9D) Relative effect of teriflunomide on peak amplitude of each fEPSP in the burst normalized to the first fEPSP amplitude (n=5, p<0.01, two-way ANOVA).
Figure 9B:
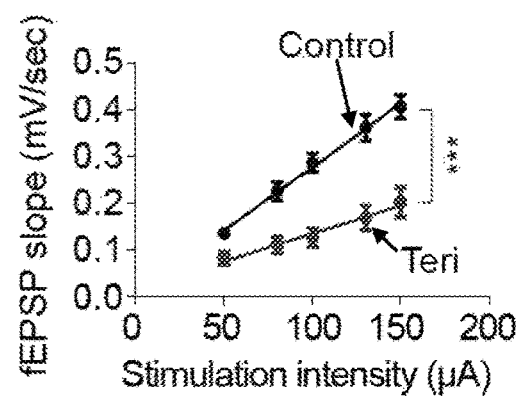

Example 10. DHODH Blockade Inhibits Basal CA3-CA1 Synaptic Transmission and Enhances Short-Term Synaptic Facilitation in Acute Hippocampal Slices Having established an essential role of DHODH activity in regulating MFR and E/I balance in hippocampal cultures, we asked whether acute DHODH inhibition modulates basal synaptic transmission in a more intact preparation—acute hippocampal slices. We evoked electrical stimulation in CA3 axons, comprising the Schaffer Collateral (SC) pathway of the hippocampus, and recorded the extracellular field excitatory postsynaptic potentials (fEPSP) in the stratum *radiatum*. We estimated the effect of teriflunomide (50 μM) on basal CA3-CA1 synaptic transmission evoked by low frequency stimulation of 0.1 Hz. Teriflunomide caused a gradual reduction in the fEPSP amplitude (FIG. 9A), resulting in a 66% decrease of the slope of input/output curve (FIG. 9B), and suggesting that DHODH blockade strongly inhibits basal synaptic transmission in CA3-CA1 hippocampal connections.

Figure 9C:
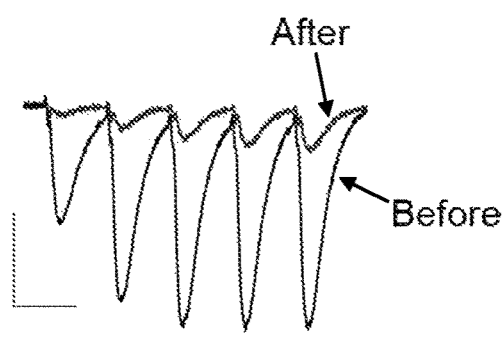
Figure 9D:
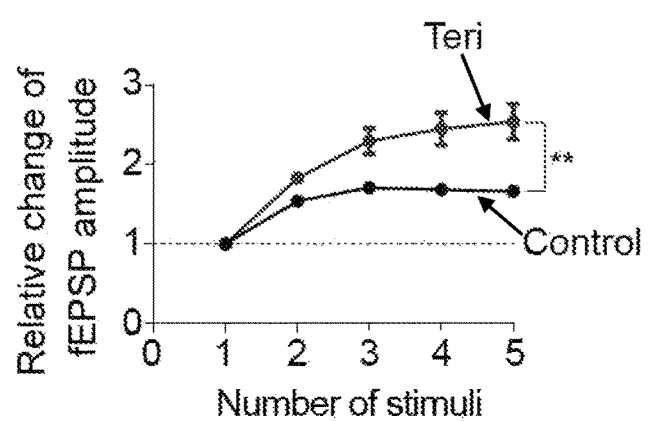

Next, we examined how DHODH inhibition affects short-term synaptic plasticity evoked by high-frequency spike bursts. This type of plasticity plays an important role in working memory function. As shown, application of teriflunomide resulted in a decrease of the first fEPSP amplitude within the burst, but its effect on the last amplitude was less pronounced (FIG. 9C). On average, teriflunomide profoundly increased short-term synaptic facilitation as estimated by increase in the relative fEPSP amplitude within the burst (FIG. 9D). These results suggest that DHODH inhibition tunes the filter properties of hippocampal synaptic connections, shifting it to high-pass filter properties.

Example 11. Intrathecal Teriflunomide Injection Enhances CA3-CA1 Short-Term Synaptic Facilitation In Vivo Finally, we used intracerebroventricular (ICV) injection of teriflunomide to test its effect on hippocampal synaptic plasticity in vivo. For this, we injected teriflunomide (100 mM/1 µl daily) for 3 consecutive days and then performed electrophysiological fEPSP recording in vivo in anesthetized (2% isoflurane) mice.

Figure 10A:
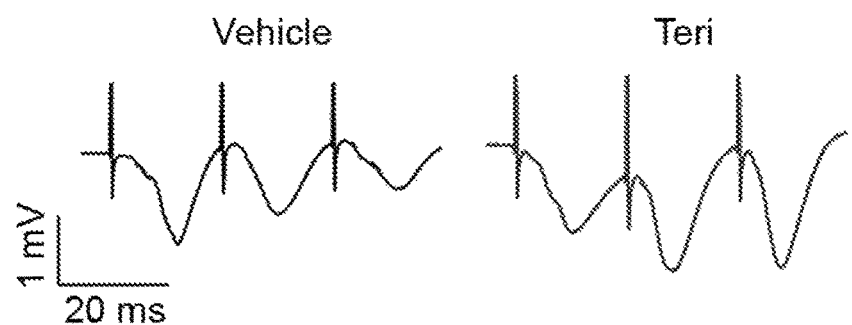
FIGS. 10A-10B show the effect of intracerebroventricular (ICV) teriflunomide injections on short-term synaptic plasticity in CA3-CA1 hippocampal connections in vivo. (10A) Representative recordings of fEPSP evoked by bursts (3 stimuli at 50 Hz) in vivo before and 60 min after ICV injection of teriflunomide (100 mM/1 μl daily, 3 days). (10B) Relative effect of teriflunomide on peak amplitude of each fEPSP in the burst normalized to the first fEPSP amplitude (n=3 per group, p<0.05, two-way ANOVA).
Figure 10B:
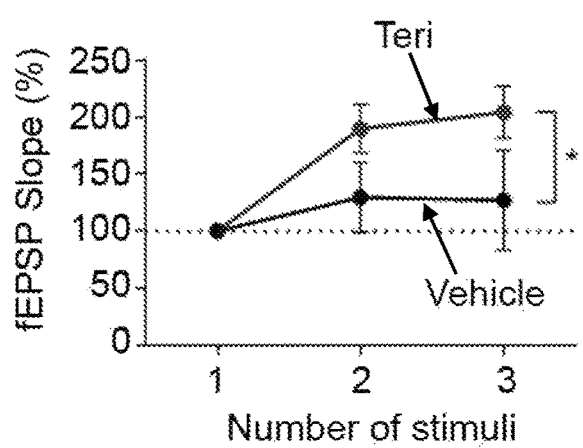

The recording electrodes were placed in the CA1 stratum radiatum, while the stimulating electrode was paced at the Schaffer Collateral fibers. We examined how inhibition of DHODH in the brain affects short-term synaptic plasticity in the hippocampus evoked by high-frequency spike bursts. ICV application of teriflunomide resulted in an increase of short-term synaptic facilitation (FIGS. 10A-B), indicating a reduction in glutamate release probability. These results suggest that intrathecal delivery of teriflunomide is effective in vivo to increase short-term synaptic facilitation.

REFERENCES

Bakker A., Krauss G. L., Albert M. S., Speck C. L., J L. R., Stark C. E., Yassa M. A., Bassett S. S., Shelton A. L., Gallagher M., Reduction of hippocampal hyperactivity improves cognition in Amnestic Mild Cognitive impairment. *Neuron*, 2012, 74, 467-474

Bar-Or A., Teriflunomide (Aubagio®) for the treatment of multiple sclerosis. *Experimental Neurology*, 2014, 262, Part A, 57-65

Berchtold N. C., Sabbagh M. N., Beach T. G., Kim R. C., Cribbs D. H., Cotman C. W., Brain gene expression patterns differentiate mild cognitive impairment from normal aged and Alzheimer's disease. *Neurobiology of Aging*, 2014, 35, 1961-1972

Bough K. J., Wetherington J., Hassel B., Pare J. F., Gawryluk J. W., Greene J. G., Shaw R., Smith Y., Geiger J. D., Dingledine R. J., Mitochondrial biogenesis in the anticonvulsant mechanism of the ketogenic diet. *Annals of Neurology*, 2006, 60, 223-235

Busche M. A., Eichhoff G., Adelsberger H., Abramowski D., Wiederhold K. H., Haass C., Staufenbiel M., Konnerth A., Garaschuk O., Clusters of hyperactive neurons near amyloid plaques in a mouse model of Alzheimer's disease. *Science*, 2008, 321, 1686-1689

Compston A., Coles A., Multiple sclerosis. *The Lancet*, 2008, 372, 1502-1517

Curia G., Longo D., Biagini G., Jones R. S., Avoli M., The pilocarpine model of temporal lobe epilepsy. *Journal of neuroscience methods*, 2008, 172, 143-157

Dickerson B. C., Salat D. H., Greve D. N., Chua E. F., Rand-Giovannetti E., Rentz D. M., Bertram L., Mullin K., Tanzi R. E., Blacker D., et al. Increased hippocampal activation in mild cognitive impairment compared to normal aging and AD. *Neurology*, 2005, 65, 404-411

Eid T., Thomas M. J., Spencer D. D., Rundén-Fran E., Lai J. C. K., Malthankar G. V., Kim J. H., Danbolt N. C., Ottersen O. P., de Lanerolle N. C., Loss of glutamine synthetase in the human epileptogenic hippocampus: possible mechanism for raised extracellular glutamate in mesial temporal lobe epilepsy. *The Lancet*, 2004, 363, 28-37

Garriga-Canut M., Schoenike B., Qazi R., Bergendahl K., Daley T. J., Pfender R. M., Morrison J. F., Ockuly J., Stafstrom C., Sutula T., Roopra A., 2-Deoxy-D-glucose reduces epilepsy progression by NRSF-CtBP-dependent metabolic regulation of chromatin structure. *Nat Neurosci*, 2006, 9, 1382-1387

Grone B. P., Baraban S. C., Animal models in epilepsy research: legacies and new directions. *Nat Neurosci*, 2015, 18, 339-343

Gulyás A. I., Buzsáki G., Freund T. F., Hirase H., Populations of hippocampal inhibitory neurons express different levels of cytochrome c. *European Journal of Neuroscience*, 2006, 23, 2581-2594

Hengen K. B., Lambo M. E., Van Hooser S. D., Katz D. B., Turrigiano G. G., Firing rate homeostasis in visual cortex of freely behaving rodents. *Neuron*, 2013, 80, 335-342

Henry T. R., Mazziotta J. C., Engel J., Christenson P. D., Zhang J. X., Phelps M. E., Kuhl D. E., Quantifying interictal metabolic activity in human temporal lobe epilepsy. *Journal of Cerebral Blood Flow & Metabolism*, 1990, 10, 748-757

Koh M. T., Haberman R. P., Foti S., McCown T. J., Gallagher M., Treatment strategies targeting excess hippocampal activity benefit aged rats with cognitive impairment. *Neuropsychopharmacology*, 2010, 35, 1016-1025

Krook-Magnuson E., Soltesz I., Beyond the hammer and the scalpel: selective circuit control for the epilepsies. *Nat Neurosci*, 2015, 18, 331-338

Kunz L., Schroder T. N., Lee H., Montag C., Lachmann B, Sariyska R., Reuter M., Stirnberg R., Stocker T., Messing-Floeter P. C., et al. Reduced grid-cell-like representations in adults at genetic risk for Alzheimer's disease. *Science*, 2015, 350, 430-433

Lam A. D., Deck G., Goldman A., Eskandar E. N., Noebels J., Cole A. J., Silent hippocampal seizures and spikes identified by foramen ovale electrodes in Alzheimer's disease. *Nat Med.*, 2017, 23(6), 678-680

Leite J. P., Garcia-Cairasco N., Cavalheiro, E. A., New insights from the use of pilocarpine and kainate models. *Epilepsy research*, 2002, 50, 93-103

Loscher W., Schmidt D., Modern antiepileptic drug development has failed to deliver: ways out of the current dilemma. *Epilepsia*, 2011, 52, 657-678

Lutas A., Yellen G., The ketogenic diet: metabolic influences on brain excitability and epilepsy. *Trends in Neurosciences*, 2013, 36, 32-40

Mazzuferi M., Kumar G., Rospo C., Kaminski R. M., Rapid epileptogenesis in the mouse pilocarpine model: video-EEG, pharmacokinetic and histopathological characterization. *Experimental neurology*, 2012, 238, 156-167

Miller S. L., Fenstermacher E., Bates J., Blacker D., Sperling R. A., Dickerson B. C., Hippocampal activation in adults with mild cognitive impairment predicts subsequent cognitive decline. *Journal of neurology, neurosurgery, and psychiatry*, 2008, 79, 630-635

Minkeviciene R., Rheims S., Dobszay M. B., Zilberter M., Hartikainen J., Fulop L., Penke B., Zilberter Y., Harkany T., Pitkanen A., Tanila H., Amyloid beta-induced neuronal hyperexcitability triggers progressive epilepsy. *The Journal of Neuroscience*, 2009, 29, 3453-3462

Oberhardt M. A., Yizhak K., Ruppin E., Metabolically re-modeling the drug pipeline. *Current opinion in pharmacology*, 2013, 13, 778-785

Palop J. J., Chin J., Roberson E. D., Wang J., Thwin M. T., Bien-Ly N., Yoo J., Ho K. O., Yu G. Q., Kreitzer A., et al. Aberrant excitatory neuronal activity and compensatory remodeling of inhibitory hippocampal circuits in mouse models of Alzheimer's disease. *Neuron,* 2007, 55, 697-711

Palop J. J., Mucke L., Epilepsy and cognitive impairments in Alzheimer disease. *Arch Neurol,* 2009, 66, 435-440

Paz J. T., Huguenard J. R., Microcircuits and their interactions in epilepsy: is the focus out of focus? *Nat Neurosci,* 2015, 18, 351-359

Petroff O. A. C., Errante L. D., Rothman D. L., Kim J. H., Spencer D. D., Glutamate-glutamine cycling in the epileptic human hippocampus. *Epilepsia,* 2002, 43, 703-710

Pitkänen A., Sutula T. P., Is epilepsy a progressive disorder? Prospects for new therapeutic approaches in temporal-lobe epilepsy. *The Lancet Neurology,* 2002, 1, 173-181

Sada N., Lee S., Katsu T., Otsuki T., Inoue T., Targeting LDH enzymes with a stiripentol analog to treat epilepsy. *Science,* 2015, 347, 1362-1367

Sanchez P. E., Zhu L., Verret L., Vossel K. A., Orr A. G., Cirrito J. R., Devidze N., Ho K., Yu G. Q., Palop J. J., Mucke L., Levetiracetam suppresses neuronal network dysfunction and reverses synaptic and cognitive deficits in an Alzheimer's disease model. *Proceedings of the National Academy of Sciences,* 2012, 109, E2895-E2903

Slomowitz E., Styr B., Vertkin I., Milshtein-Parush H., Nelken I., Slutsky M., Slutsky I., Interplay between population firing stability and single neuron dynamics in hippocampal networks. *Elife,* 2015, 4

Sperling R. A., LaViolette P. S., O'Keefe K., O'Brien J., Rentz D. M., Pihlajamaki M., Marshall G., Hyman B. T., Selkoe D. J., Hedden T., et al. Amyloid deposition Is associated with impaired default network function in older persons without dementia. *Neuron,* 2009, 63, 178-188

Verret L., Mann E. O., Hang G. B., Barth A. M. I., Cobos I., Ho K., Devidze N., Masliah E., Kreitzer A. C., Mody I., et al. Inhibitory interneuron deficit links altered network activity and cognitive dysfunction in Alzheimer model. *Cell,* 2012, 149, 708-721

Vossel K. A., Beagle A. J., Rabinovici G. D., Shu H., Lee S. E., Naasan G., Hedge M., Comes S. B., Henry M. L., Nelson A. B., Seeley W. W., Geschwind M. D., Gorno-Tempini M. L., Shin T., Kirsh H. E., Garcia P. A., Miller N. L., Mucke L., Seizures and epileptiform activity in the early stages of Alzheimer disease. *JAMA Neurol.,* 2013, 70(9), 1158-1166

Vossel K. A., Ranasinghe K. G., Beagle A. J., Mizuiri D., Honma S. M., Dowling A. F., Darwish S. M., Van Berto V., Barnes D. E., Mantle M., Karydas A. M., Coppola G., Roberson D. E., Miller B. L., Garcia P. A., Kirsh H. E., Mucke L., Nagarajan S. S., Incidence and impact of subclinical epileptiform activity in Alzheimer's disease. *Ann Neurol.,* 2016, 80(6), 858-870

Whittaker R. G., Turnbull D. M., Whittington M. A., Cunningham M. O., Impaired mitochondrial function abolishes gamma oscillations in the hippocampus through an effect on fast-spiking interneurons. *Brain,* 2011, 134, e180-e180

Wilcox K. S., Dixon-Salazar T., Sills G. J., Ben-Menachem E., White H. S., Porter R. J., Dichter M. A., Moshé S. L., Noebels J. L., Privitera M. D., Rogawski M. A. Issues related to development of new anti-seizure treatments. *Epilepsia,* 2013, 54, 24-34

Yassa M. A., Stark S. M., Bakker A., Albert M. S., Gallagher M., Stark C. E. L., High-resolution structural and functional MRI of hippocampal CA3 and dentate gyrus in patients with amnestic Mild Cognitive Impairment. *NeuroImage,* 2010, 51, 1242-1252

Yizhak K., Gabay O., Cohen H., Ruppin E., Model-based identification of drug targets that revert disrupted metabolism and its application to ageing. *Nat Commun,* 2013, 4

---

What is claimed is:

1. A method for treating a disease or disorder associated with cortico-hippocampal hyperactivity and selected from the group consisting of epilepsy in a subject in need thereof, or for preventing or delaying onset of said disease or disorder in a subject diagnosed as suffering from an elevated cortico-hippocampal activity or being at genetic risk for developing said disease or disorder, said method comprising administering to said subject a therapeutically effective amount of an active agent capable of reducing dihydroorotate dehydrogenase (DHODH) enzyme activity in the central nervous system (CNS) of said subject, optionally together with a pyrimidine nucleobase or an intermediate in the de novo synthesis thereof,
   wherein said active agent comprises a nucleic acid molecule that reduces the gene expression level of DHODH enzyme, said nucleic acid molecule comprising an shRNA or artificial siRNA molecule comprising a nucleic acid sequence being complementary to a sequence within a nucleic acid sequence encoding said DHODH enzyme, or a nucleic acid molecule encoding said artificial siRNA or shRNA molecule; or said active agent is (2Z)-2-cyano-3-hydroxy-N-[4-(trifluoromethyl)phenyl]but-2-enamide (teriflunomide) or a pharmaceutically acceptable salt thereof,
   provided that when said active agent is administered without said pyrimidine nucleobase or intermediate in the de novo synthesis thereof, said subject does not suffer from multiple sclerosis.

2. The method of claim 1, wherein said DHODH enzyme is a human DHODH enzyme.

3. The method of claim 1, wherein said shRNA or siRNA molecule comprises a nucleic acid sequence being perfectly complementary to a sequence within said nucleic acid sequence encoding said DHODH enzyme.

4. The method of claim 1, wherein said active agent is a vector comprising said nucleic acid molecule.

5. The method of claim 4, wherein said vector is a modified virus derived from a virus selected from retrovirus, adenovirus, adeno-associated virus, pox virus, alphavirus, herpes virus, or lentivirus.

6. The method of claim 5, wherein said vector is a modified virus derived from a lentivirus.

7. The method of claim 4, wherein said vector comprises a nucleic acid molecule encoding an shRNA molecule comprising a nucleic acid sequence being complementary to a sequence within a nucleic acid sequence encoding said DHODH enzyme.

8. The method of claim 1, wherein said active agent is teriflunomide, or a pharmaceutically acceptable salt thereof.

9. The method of claim 1, wherein said intermediate in the de novo synthesis of pyrimidine nucleobases is uridine, uridine monophosphate (UMP), cytidine, cytidine monophosphate (CMP), deoxythymidine, or deoxythymidine monophosphate (dTMP).

10. The method of claim 1, wherein said active agent is teriflunomide or a pharmaceutically acceptable salt thereof, and it is administered in combination with said pyrimidine nucleobase or an intermediate in the de novo synthesis thereof.

11. The method of claim 10, wherein said pyrimidine nucleobase or intermediate in the de novo synthesis thereof is uridine, UMP, cytidine, CMP, deoxythymidine, or dTMP.

12. The method of claim 1, wherein said active agent is teriflunomide or a pharmaceutically acceptable salt thereof, and it is administered without said pyrimidine nucleobase or an intermediate in the de novo synthesis thereof.

13. The method of claim 1, wherein said active agent is administered intrathecally.

14. The method of claim 1, wherein the disease or disorder is selected from the group consisting of temporal lobe epilepsy (TLE) and Dravet syndrome.

15. The method of claim 1, wherein the subject is at risk of sudden unexplained death in epilepsy (SUDEP).

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: synthetic Sequence

<400> SEQUENCE: 1
cgacggactg atcatcacaa a                                              21

<210> SEQ ID NO 2
<211> LENGTH: 21
<212> TYPE: DNA
<213> ORGANISM: Artificial Sequence
<220> FEATURE:
<223> OTHER INFORMATION: synthetic Sequence

<400> SEQUENCE: 2
cgaccatttc tacgccgagt a                                              21

<210> SEQ ID NO 3
<211> LENGTH: 21
<212> TYPE: DNA
<213> ORGANISM: Artificial Sequence
<220> FEATURE:
<223> OTHER INFORMATION: synthetic Sequence
```

```
<400> SEQUENCE: 3
cgaccatttc tacgccgagt a                                              21

<210> SEQ ID NO 4
<211> LENGTH: 21
<212> TYPE: DNA
<213> ORGANISM: Artificial Sequence
<220> FEATURE:
<223> OTHER INFORMATION: synthetic Sequence

<400> SEQUENCE: 4
gcagactatg tagagggtgt t                                              21

<210> SEQ ID NO 5
<211> LENGTH: 21
<212> TYPE: DNA
<213> ORGANISM: Artificial Sequence
<220> FEATURE:
<223> OTHER INFORMATION: synthetic Sequence

<400> SEQUENCE: 5
cggactctat aagctgggct t                                              21

<210> SEQ ID NO 6
<211> LENGTH: 21
<212> TYPE: DNA
<213> ORGANISM: Artificial Sequence
<220> FEATURE:
<223> OTHER INFORMATION: synthetic Sequence

<400> SEQUENCE: 6
ccactgtctc tagatctaaa t                                              21

<210> SEQ ID NO 7
<211> LENGTH: 21
<212> TYPE: DNA
<213> ORGANISM: Artificial Sequence
<220> FEATURE:
<223> OTHER INFORMATION: synthetic Sequence

<400> SEQUENCE: 7
cctgggccat aaattccgaa a                                              21

<210> SEQ ID NO 8
<211> LENGTH: 21
<212> TYPE: DNA
<213> ORGANISM: Artificial Sequence
<220> FEATURE:
<223> OTHER INFORMATION: synthetic Sequence

<400> SEQUENCE: 8
gaggaccaag ctgttattaa c                                              21

<210> SEQ ID NO 9
<211> LENGTH: 21
<212> TYPE: DNA
<213> ORGANISM: Artificial Sequence
<220> FEATURE:
<223> OTHER INFORMATION: synthetic Sequence

<400> SEQUENCE: 9
tgagctggag gcccttctaa a                                              21

<210> SEQ ID NO 10
<211> LENGTH: 21
```

```
<212> TYPE: DNA
<213> ORGANISM: Artificial Sequence
<220> FEATURE:
<223> OTHER INFORMATION: synthetic Sequence

<400> SEQUENCE: 10
tgggctgcct ctgggaataa a                                              21
```